US012758271B2

(12) United States Patent
Biedermann et al.

(10) Patent No.: US 12,758,271 B2
(45) Date of Patent: Oct. 13, 2026

(54) BONE ANCHORING DEVICE FOR COUPLING A ROD TO A BONE ANCHORING ELEMENT

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Bernd Fischer, Friedenweiler (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/425,119

(22) Filed: Dec. 18, 2025

(65) Prior Publication Data

US 2026/0174473 A1 Jun. 25, 2026

Related U.S. Application Data

(60) Provisional application No. 63/737,971, filed on Dec. 23, 2024.

(30) Foreign Application Priority Data

Dec. 23, 2024 (EP) .................................... 24223006

(51) Int. Cl.

*A61B 17/70* (2006.01)
*A61B 17/86* (2006.01)
*A61B 90/00* (2016.01)

(52) U.S. Cl.

CPC ...... *A61B 17/7035* (2013.01); *A61B 17/8625* (2013.01); *A61B 90/03* (2016.02); *A61B 2090/034* (2016.02)

(58) Field of Classification Search

None

See application file for complete search history.

(56) References Cited

U.S. PATENT DOCUMENTS 7,749,258 B2 7/2010 Biedermann et al.
7,892,259 B2 2/2011 Biedermann et al.
(Continued)

FOREIGN PATENT DOCUMENTS

EP 4 437 983 A1 10/2024

OTHER PUBLICATIONS

Extended European Search Report for Application No. 24223006.8, dated Jun. 11, 2025, 11 pages.

*Primary Examiner* — Tessa M Matthews

(74) *Attorney, Agent, or Firm* — Womble Bond Dickinson (US) LLP

(57) ABSTRACT

A bone anchoring device includes a bone anchoring element, a receiving part having an accommodation space for pivotably accommodating a head of the bone anchoring element, a pressure element movable in the receiving part to engage and exert pressure on the head to clamp the head at an angular position relative to the receiving part, and at least one restraining element separate from the pressure element and positionable in the receiving part. The pressure element defines at least one opening that provides access laterally through the pressure element to the head in the receiving part. The restraining element is movable relative to the pressure element to engage the head laterally through the opening of the pressure element to restrict the pivoting of the head in at least one radial direction while the head remains pivotable in at least one other radial direction.

20 Claims, 12 Drawing Sheets

(56) References Cited

U.S. PATENT DOCUMENTS

| | | | | |
|---|---|---|---|---|
| 8,353,932 | B2 * | 1/2013 | Jackson | A61B 17/702 606/246 |
| 10,610,265 | B1 * | 4/2020 | Ark | A61B 17/7052 |
| 11,096,727 | B2 | 8/2021 | Barrus et al. | |
| 2010/0305621 | A1 | 12/2010 | Wang et al. | |
| 2011/0257690 | A1 * | 10/2011 | Rezach | A61B 17/7037 606/302 |
| 2017/0311988 | A1 * | 11/2017 | Petit | A61B 17/7038 |
| 2018/0008319 | A1 | 1/2018 | Chao et al. | |
| 2018/0168397 | A1 * | 6/2018 | Colston | A47J 37/0704 |
| 2022/0087721 | A1 | 3/2022 | Yacoub | |
| 2024/0156497 | A1 | 5/2024 | Biedermann et al. | |

* cited by examiner

BONE ANCHORING DEVICE FOR COUPLING A ROD TO A BONE ANCHORING ELEMENT

CROSS-REFERENCE TO RELATED APPLICATION(S)

The present application claims priority to and the benefit of U.S. Provisional Patent Application No. 63/737,971 , filed Dec. 23, 2024, the contents of which are hereby incorporated by reference in their entirety, and claims priority from European Patent Application EP 24 223 006.8, filed Dec. 23, 2024, the contents of which are hereby incorporated by reference in their entirety.

BACKGROUND

Field

The present application relates to a bone anchoring device including a bone anchoring element and a coupling device for coupling a rod to the bone anchoring element. In particular, the bone anchoring device is a modular bone anchoring device that can be selectively adapted for various clinical requirements.

Description of Related Art

Bone anchoring devices including a bone anchoring element and a receiving part are used in orthopaedic surgery, in particular in spinal surgery, for coupling a rod to the bone anchoring element when the bone anchoring element is anchored to bone or a vertebra, and for connecting several bone anchoring devices using the rod. In a polyaxial bone anchoring device, a head of the bone anchoring element is pivotably received in the receiving part, so that the receiving part can assume various angular positions in multiple different planes with respect to the bone anchoring element. Thus, a suitable orientation of the bone anchoring element with respect to the rod can be achieved.

Depending on the use or clinical application, it can be desirable to provide a bone anchoring device configured to restrict pivoting of the bone anchoring element with respect to the receiving part, for example, to a single plane, i.e., a uniplanar bone anchoring device, or to provide a monoaxial bone anchoring device in which the shank has a fixed angle, preferably a zero-angle, with respect to the receiving part.

Various designs of uniplanar bone anchoring devices are known in which the shank of the bone anchoring element can pivot in the receiving part only in a single plane. For example, U.S. Pat. No. 7,749,258 B2 describes a uniplanar bone anchoring device including a receiving part for receiving a rod, a pressure element, and a bone anchoring element being moveable relative to the receiving part in a limited angular range about the longitudinal axis of the receiving part, the angles lying in a single plane. The movement of the bone anchoring element relative to the receiving part is limited by a form-fit connection including cooperating guiding surfaces at the head of the bone anchoring element and at the pressure element.

U.S. Pat. No. 7,892,259 B2 describes a bone anchoring device including a receiving part having a bore and an anchoring element having a head positionable within the bore, the head having a spherically shaped surface portion and recessed surface portions. Pins are insertable into through-holes formed in the receiving part to engage the recessed surface portions of the head, such that the anchoring element is pivotable relative to the receiving part around a single axis of rotation.

SUMMARY

There is still a need to provide a bone anchoring device having a simple structure with only few parts, that may facilitate implementation of at least a polyaxial and/or a uniplanar and/or a monoaxial bone anchoring device. Thus, it is an object underlying the invention to provide a bone anchoring device that can be used in a modular manner, enabling a selectable functionality in terms of a polyaxial, a monoaxial, and/or a uniplanar design.

According to an embodiment of the invention, a bone anchoring device is provided that includes a bone anchoring element having a shank for anchoring to bone and a head, and a coupling device for coupling a rod to the bone anchoring element. The coupling device includes a receiving part having a first end, an opposite second end, and a passage extending between the first end and the second end, the passage defining a central axis, where the receiving part has an accommodation space at the second end for accommodating the head of the bone anchoring element. The coupling device further includes a pressure element configured to be arranged in the passage of the receiving part and to exert pressure onto the head in the accommodation space to clamp the head at a particular angular position relative to the receiving part, where the pressure element has at least one opening that provides access to the inserted head from a direction transverse to the central axis, and at least one restraining element or designated restriction element configured to be arranged in the passage of the receiving part, where the restraining element is movable relative to the pressure element in an axial direction between a first position and a second position, and where at the second position, the restraining element contacts the inserted head through the opening of the pressure element to restrict pivoting of the inserted head relative to the receiving part.

Transverse to the central axis means that the direction at which the inserted head is accessible is arranged at an angle relative to the central axis, preferably the direction is substantially perpendicular, further preferably perpendicular, to the central axis.

Preferably, when the restraining element is at the first position, the restraining element may be free from any interaction with the inserted head, i.e., the restraining element does not act upon the inserted head, and/or when the restraining element is at the second position, the restraining element may directly contact the inserted head to restrict pivoting of the head relative to the receiving part. For example, when the restraining element is at the first position, the resulting bone anchoring device may be a polyaxial bone anchoring device, and when the restraining element is at the second position, the resulting bone anchoring device may be a uniplanar bone anchoring device. More generally, the restraining element may have a first restraining surface and the head may have a second restraining surface configured to cooperate with the first restraining surface to reduce a degree of freedom of pivoting of the head with respect to the receiving part.

With the bone anchoring device according to embodiments of the invention, it is possible to selectively use the bone anchoring device as a polyaxial bone anchoring device or as a uniplanar bone anchoring device. The uniplanar bone anchoring device can be implemented by applying at least one restraining element to restrict the pivoting motion of the head relative to the receiving part, for example, to a single plane. This can be carried out at any time before surgery. Thus, the bone anchoring device requires only few parts, and the inventory required for surgery can be reduced, while providing a variety of different possible applications.

Since the receiving part may be more expensive and/or more difficult to manufacture compared to the bone anchoring element, the manufacturing costs and/or the costs for stock holding can be decreased if the same receiving part or coupling device can be used for a polyaxial or a uniplanar application.

Preferably, the restraining element is only accessible within the passage from above, i.e., from the first end of the receiving part. An axial displacement of the restraining element may be effected by an instrument that enters the passage of the receiving part to act upon the restraining element. In particular, the restraining element may not be accessible or actuatable laterally from the outside of the receiving part, i.e., in a direction transverse to the central axis.

Preferably, the receiving part and/or the pressure element and/or the restraining element is each a monolithic piece.

According to a further embodiment, a bone anchoring device is provided that includes a bone anchoring element having a shank for anchoring to bone and a head, and a coupling device for coupling a rod to the bone anchoring element. The coupling device includes a receiving part having a first end, an opposite second end, and a passage extending between the first end and the second end, the passage defining a central axis, where the receiving part has an accommodation space at the second end for accommodating the head of the bone anchoring element. The coupling device further includes a pressure element configured to be arranged in the passage of the receiving part and to exert pressure onto the head in the accommodation space to clamp the head at a particular angular position relative to the receiving part, and a plug member that is configured to cooperate with the inserted head of the bone anchoring element, such that the plug member forms a monoaxial connection in which the bone anchoring element is prevented from pivoting relative to the receiving part.

This makes it possible to use a bone anchoring device that has been originally designed as a polyaxial or uniplanar bone anchoring device for various monoaxial applications, such as trauma applications, growing rod applications, posterior scoliosis correction, anterior scoliosis surgery, or anterior scoliosis tethering.

BRIEF DESCRIPTION OF THE DRAWINGS

Further features and advantages will become apparent from the description of embodiments by means of the accompanying drawings. In the drawings.

DETAILED DESCRIPTION

Figure 1:
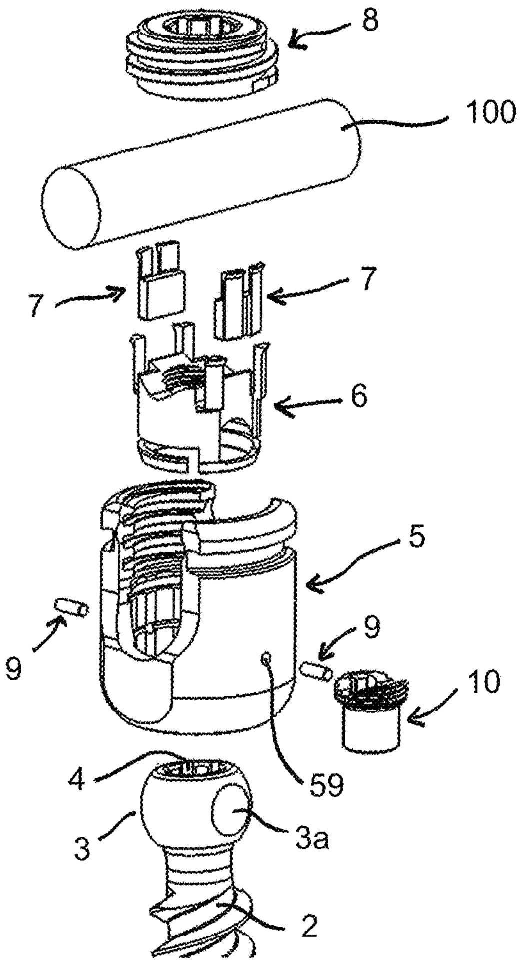
FIG. 1 shows an exploded perspective view of a bone anchoring device according to a first embodiment.

With reference to FIGS. 1 to 18*d*, a first embodiment of a bone anchoring device is described. As shown in particular in FIGS. 1 to 3, the bone anchoring device includes a bone anchoring element 1 having a shank 2 for anchoring in bone or in a vertebra and a head 3. The shank 2 defines a shank axis S, and has a bone engagement feature, such as a thread. Further, the bone anchoring device includes a receiving part 5 for receiving the head 3 of the bone anchoring element 1 and for receiving a rod 100 that is configured to connect several bone anchoring devices. A pressure element 6 is configured to be arranged within the receiving part 5 for exerting pressure onto the head 3 of the bone anchoring element 1, and for clamping the head 3 with the shank 2 at a particular angular position relative to the receiving part 5.

Two restraining elements 7 are configured to be arranged within the receiving part 5 so as to be movable relative to the pressure element 6 between a first position and a second position in the axial direction. At the first position, the restraining elements do not act upon the inserted head 3. In particular, when the restraining elements 7 are at the first position, the shank 2 of the bone anchoring element 1 may be pivotable in multiple different planes relative to the receiving part 5, i.e., the resulting bone anchoring device is a polyaxial bone anchoring device. When the restraining elements 7 are at the second position, the restraining elements may directly contact the inserted head 3 to restrict pivoting of the shank 2 relative to the receiving part 5 within a single plane, i.e., the resulting bone anchoring device is a uniplanar or monoplanar bone anchoring device. The single pivot plane may be defined by the cooperation of a first restraining surface provided at the restraining elements 7 and a second restraining surface provided at the head 3, as described further below. Optionally, a plug member 10 is provided that is configured to be inserted into the pressure element 6 and to cooperate with the head 3 such that the bone anchoring element 1 is prevented from pivoting relative to the receiving part 5, i.e., the resulting bone anchoring device is a monoaxial bone anchoring device.

Further, in order to secure the pressure element 6 against rotation, two pins 9 are provided that are insertable into transverse through-holes 59 provided at the receiving part 5. To lock the head 3 and the rod 100 in the receiving part 5, a locking element 8 in the form of, for example, an inner screw or set screw is provided.

The head 3 of the bone anchoring element 1 has a spherically-shaped outer surface portion and two second restraining surfaces in the form of substantially planar or flat surface portions 3*a* provided at the outer surface portion that are configured to cooperate with the first restraining surfaces of the restraining elements 7. The planar surface portions 3*a* provide for a reduced diameter of the head 3 as compared to a diameter defined by the spherically-shaped outer surface portion, i.e., they are recessed from a sphere defined by the spherically-shaped outer surface portion. The planar surface portions 3*a* are located at opposite sides of the head and are offset at 180° from one another. A plane of the planar surface portions 3*a* may be substantially parallel to the shank axis S, and the two planar surface portions 3*a* may be substantially parallel to one another.

The head 3 further has at its free end, opposite to the shank 2, an engagement recess 4 for engagement with a tool, such as a driver.

Referring in addition to FIGS. 4 to 7, the receiving part 5 is described in greater detail. The receiving part 5, which may be a monolithic piece, has a first end or top end 5*a* and a second end or bottom end 5*b* opposite to the top end 5*a*. In general, the receiving part 5 may have a substantially cylindrical outer shape with a central longitudinal axis C extending through the top end 5*a* and the bottom end 5*b*. Coaxially to the central axis C, a passage 51 is provided within the receiving part, the passage extending from the top end 5*a* to the bottom end 5*b* and forming an opening 52 at the bottom end 5*b*. At a distance from the top end 5*a*, the passage 51 widens into an accommodation space 53 that is configured to receive the head 3 and at least a portion of the pressure element 6 therein. Adjacent to the opening 52 at the bottom end 5*b*, the accommodation space 53 narrows towards the opening 52 in a narrowing portion 53*a*, which may be, for example, a tapered, and more particularly a conical, surface that may cooperate with a corresponding surface of the pressure element 6. The width of the opening 52 may be greater than the greatest diameter of the head 3, so that the head 3 may be inserted from the bottom end 5*b* into the accommodation space 53. To enable the insertion of the head 3 from the bottom end 5*b*, the width of the accommodation space 53 is such that the pressure element 6 can expand therein to permit the insertion of the head 3.

The receiving part 5 further has a substantially U-shaped recess 54 that extends from the top end 5*a* and in a direction towards the bottom end 5*b*. By means of the U-shaped recess 54, two free legs 55 are formed that define a channel that is open towards the first end 5*a* for receiving the rod 100. The upper part of the receiving part 5 adjacent the top end 5*a* that has the U-shaped recess 54 thus defines a rod receiving portion configured to receive the rod 100, and the lower part of the receiving part 5 adjacent the bottom end 5*b* that has the accommodation space 53 defines a head receiving portion for accommodating the head 3 of the bone anchoring element 1.

On an inner surface of the legs 55, an internal thread 56 is formed that is configured to cooperate with an outer thread of the locking element 8. A circumferential first groove 57*a* is provided at the inner wall of the legs 55 at a distance from a bottom 54*a* of the U-shaped recess 54. The first groove 57*a* provides a stop for restricting an upward movement of the pressure element 6 towards the first end 5*a* when the pressure element 6 is assembled with the receiving part 5 at an insertion position. Between the circumferential first groove 57*a* and the accommodation space 53, a circumferential second groove 57*b* is provided for engagement with a portion of the pressure element 6 to secure a pre-locking position of the pressure element 6.

At the inner surface of the receiving part 5, a recessed portion 58 is provided that extends from the first groove 57*a* in the axial direction towards the bottom end 5*b* of the receiving part 5. A shape of the recessed portion 58 is complementary to a shape of an outer surface portion of the restraining element 7, to provide for a space to at least partially receive the restraining element 7 therein and allow the restraining element to be axially displaced. The recessed portion 58 ends at a lower end at a distance from the second end 5*b* of the receiving part 5, thus forming a stop 58*b* for restricting a downward movement of the restraining element 7 towards the second end 5*b*.

In the present embodiment, two such recessed portions 58 are provided at the inner surface of the receiving part 5 and are offset at 180° from one another, each recessed portion 58 being provided on one of the legs 55 at a circumferential position approximately at the center of the respective leg 55. A position of the recessed portions 58 in the circumferential direction may be arranged at substantially 90° from a longitudinal axis L of the channel defined by the U-shaped recess 54 for receiving the rod 100.

Figure 2:
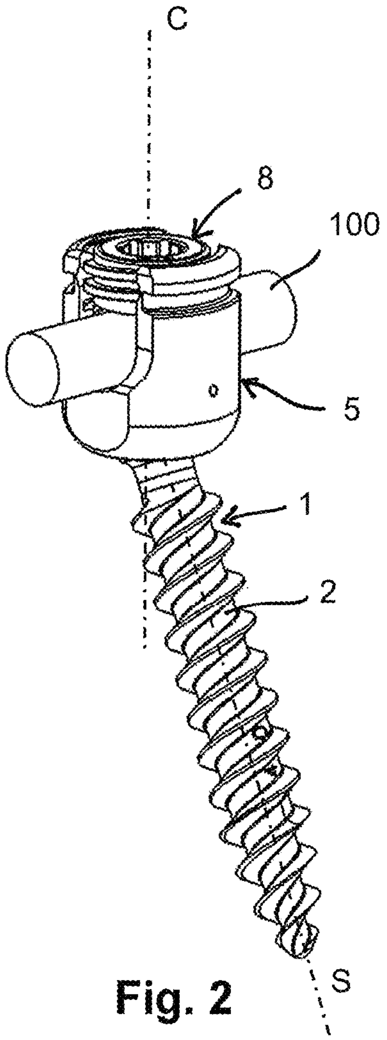
FIG. 2 shows a perspective view of the bone anchoring device of FIG. 1 in an assembled state.
Figure 3:
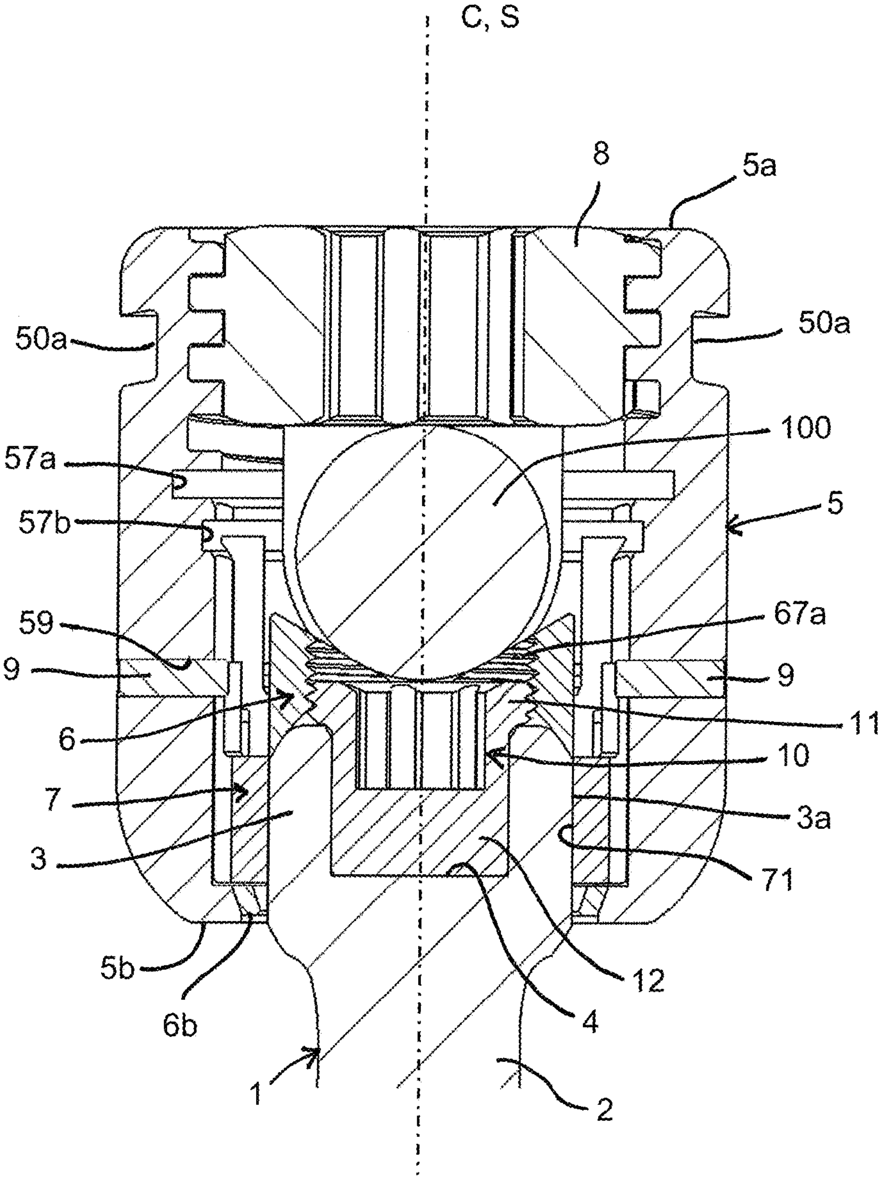
FIG. 3 shows a cross-sectional view of the bone anchoring device of FIGS. 1 and 2, the cross-section taken in a plane extending through a central axis of the bone anchoring device and perpendicular to a rod axis of an inserted rod.
Figure 4:
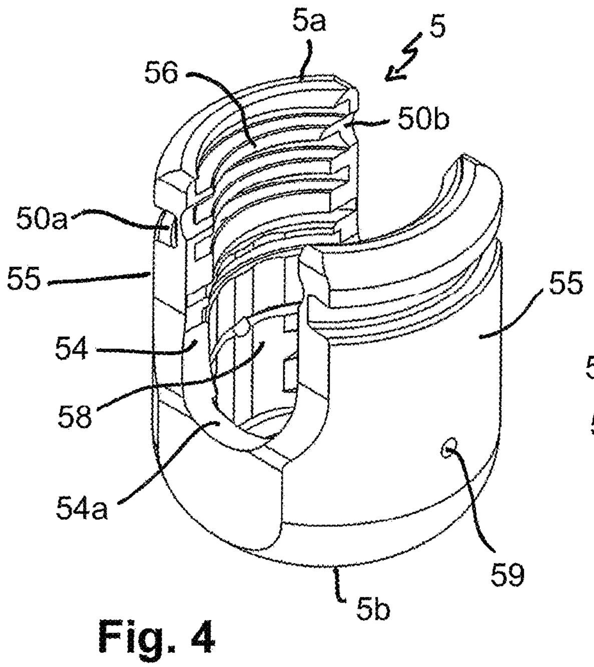
FIG. 4 shows a perspective view from above a receiving part of the bone anchoring device of FIGS. 1 to 3.
Figure 5:
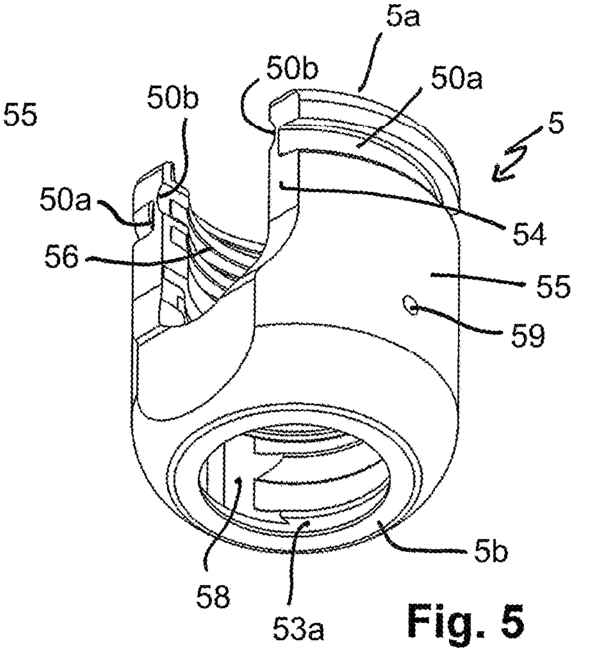
FIG. 5 shows a perspective view from below the receiving part of FIG. 4.
Figure 6:
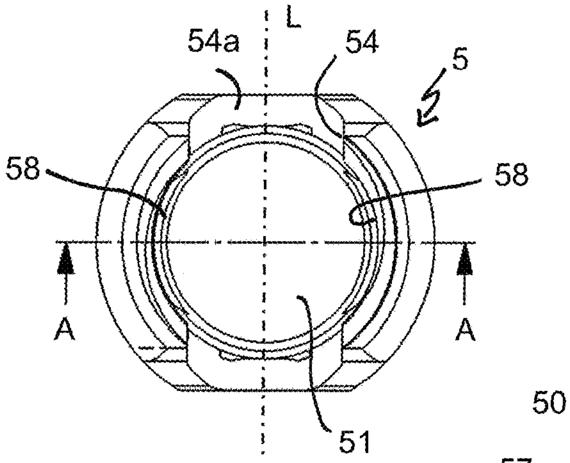
FIG. 6 shows a top view of the receiving part of FIGS. 4 and 5.
Figure 7:
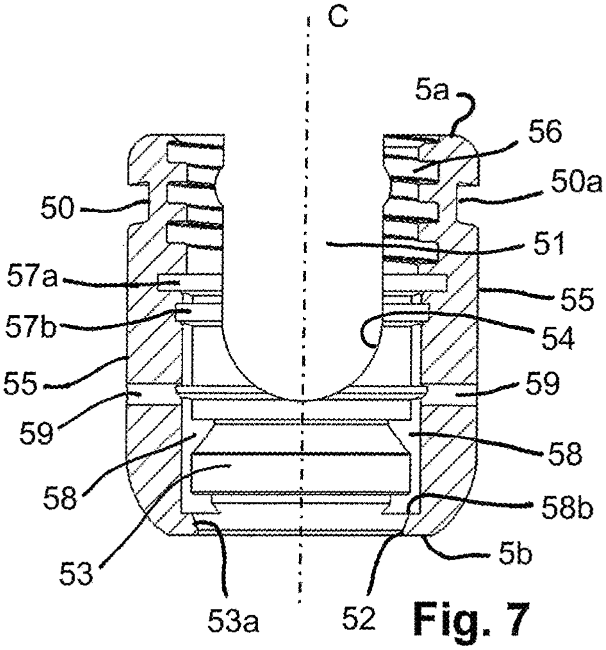
FIG. 7 shows a cross-sectional view of the receiving part of FIGS. 4 to 6, the cross-section taken along line A-A in FIG. 6.
Figure 8:
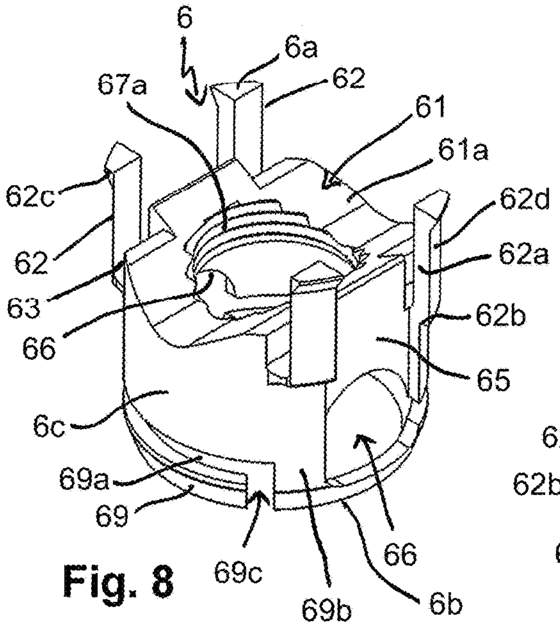
FIG. 8 shows a perspective view from above a pressure element of the bone anchoring device of FIGS. 1 to 3.
Figure 9:
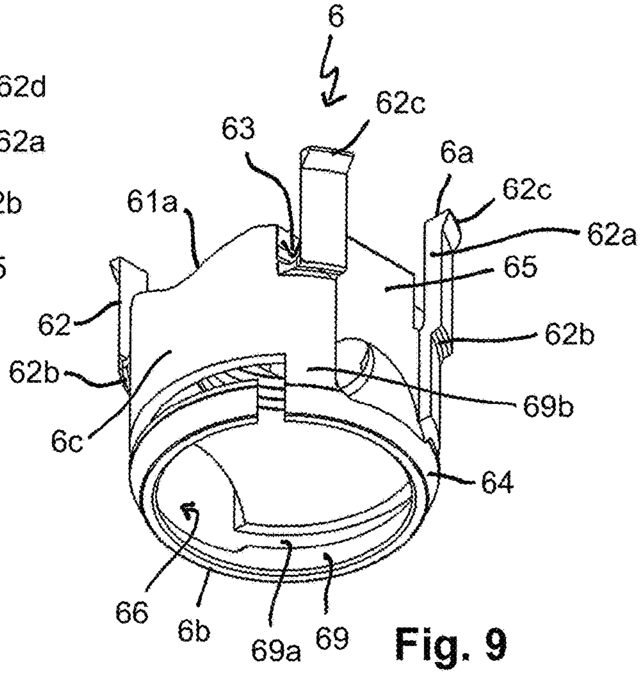
FIG. 9 shows a perspective view from below the pressure element of FIG. 8.
Figure 10:
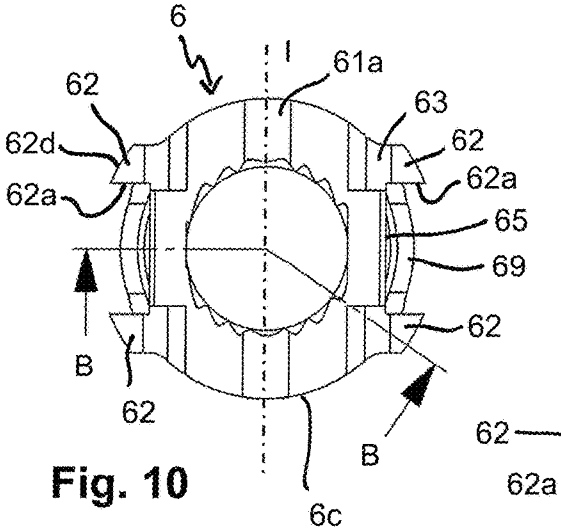
FIG. 10 shows a top view of the pressure element of FIGS. 8 and 9.
Figure 11:
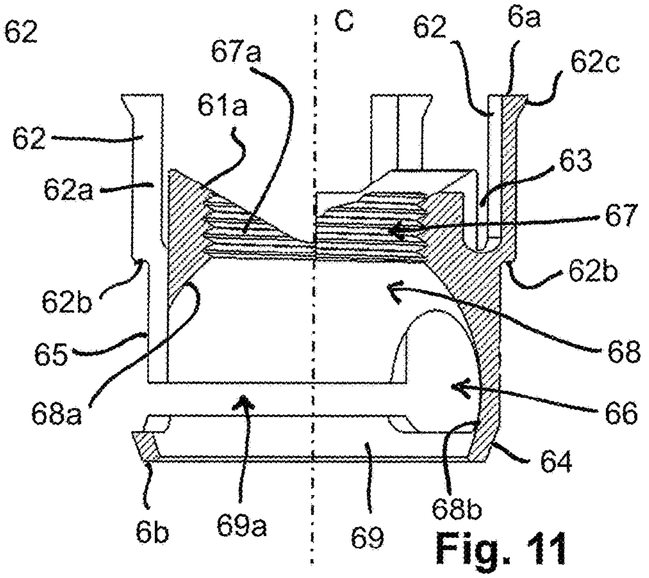
FIG. 11 shows a cross-sectional view of the pressure element of FIGS. 8 to 10, the cross-section taken along line B-B in FIG. 10.

In addition, two through-holes 59 extend through the legs 55 of the receiving part 5 in a direction perpendicular to the central axis C and at a circumferential position approximately at the center of each of the legs 55. An axial position of the through-holes 59 may be approximately at a position of the bottom 54*a* of the U-shaped recess 54. The through-holes 59 are arranged at 180° offset from each other and at 90° with respect to the longitudinal axis L of the channel defined by the U-shaped recess 54. The through-holes 59 are configured to receive the pins 9 therein, as shown in FIGS. 1 and 3. The pins 9 are configured to extend through the through-holes 59 and to engage the restraining elements 7 to secure the restraining elements 7 and the pressure element 6 against rotating.

At the outer surface of each of the legs 55, a circumferential groove 50*a* may be provided for engagement with a tool or an instrument. The groove 50*a* may be provided at a distance from the top end 5*a*, at the rod receiving portion of the receiving part 5. Alternatively or in addition, notches 50*b* may be provided at circumferential sides of the legs facing the U-shaped channel 54, which may also serve for engagement with a tool or an instrument.

Referring further to FIGS. 8 to 11, the pressure element 6 is described. The pressure element 6 may be a monolithic piece that is configured to be arranged in the passage 51 of the receiving part 5 to exert pressure onto the head when the head 3 and the pressure element 6 are in the receiving part 5, such that the head is pivotable with respect to the receiving part and can be clamped and/or locked at a particular angle relative to the receiving part.

The pressure element 6 has a first end or top end 6*a* and a second end or bottom end 6*b*, and may be substantially cylindrical, with an outer diameter that allows the pressure element 6 to move in the passage 51 of the receiving part 5. At the top end 6*a*, a rod receiving recess 61 is formed with a rod support surface 61*a*. The rod support surface 61*a* may have a substantially V-shaped cross-section, with a longitudinal axis l extending substantially perpendicular to a cylinder axis of the pressure element 6 that coincides with the central axis C of the receiving part 5 when the pressure element 6 is in the receiving part 5. The depth of the rod receiving recess 61 may be smaller than a diameter of the rod 100. Hence, when the rod 100 rests on the rod support surface 61*a*, the rod 100 projects over the top end 6*a* of the pressure element as shown, for example, in FIG. 3. The V-shape of the rod support surface 61*a* more easily and robustly facilitates use of rods with different diameters.

The pressure element has a central bore extending from the rod receiving recess 61 to the bottom end 6*b*, the bore having an upper portion 67 adjacent the rod receiving recess 61 that widens into a head receiving portion 68 adjacent the bottom end 6*b*. The upper portion 67 of the bore may be substantially cylindrical, with a diameter smaller than a diameter of the head receiving portion 68. Optionally, an engagement structure in the form of an internal thread 67*a* is provided at the inner surface of the upper portion 67 that is configured to cooperate with an external thread provided at the plug member 10. The head receiving portion 68 is configured to receive the head 3 of the bone anchoring element 1 therein, and forms an opening at the bottom end 6*b* for inserting the head 3. In greater detail, the head receiving portion 68 includes an upper spherical section 68*a* adjacent the upper portion 67 of the central bore that widens towards the bottom end 6*b*, and a lower spherical section 68*b* at the bottom end 6*b* that narrows towards the bottom end 6*b*. The upper and lower spherical sections 68*a*, 68*b* are shaped so as to matingly receive the spherical head 3 therein, to encompass the head 3 laterally and from a free end of the head, and to cover a portion of the head including a largest diameter of the head.

The pressure element 6 further includes four arms 62 that are arranged in pairs on opposite sides of the rod receiving recess 61. A distance between two of the arms 62 on the same side of the rod receiving recess 61 is such that the restraining element 7 can be received between the two arms 62, and preferably contacts respective sidewalls 62*a* of the arms 62 to be guided by the sidewalls 62*a* when displaced in the axial direction. Each arm 62 extends axially between the top end 6*a* of the pressure element 6 and a bottom end 62*b* of the arm 62, with the bottom end 62*b* being closer axially to the rod support surface 61*a* than to the bottom end 6*b* of the pressure element 6.

Each arm 62 is provided further radially away from the central axis C than a cylindrical outer surface portion 6*c* of the pressure element 6, so that a gap 63 is formed between the arm 62 and the outer surface portion 6*c* of the pressure element 6. Hence, by the bottom end 62*b* of the arm 62, a step may be formed where the arm protrudes away from the outer surface portion 6*c* of the pressure element 6. The gap 63 formed between the arm 62 and the outer surface portion 6*c* of the pressure element 6 renders the arm 62 resilient in a direction transverse to the longitudinal axis l of the rod support surface 61*a*.

A free end of the arms 62 may have a radially protruding rim 62*c*, an upper surface of which forms the top end 6*a* of the pressure element 6. The rim 62*c* is configured to engage the circumferential grooves 57*a*, 57*b* provided at the inner surface of the legs 55 of the receiving part 5 to secure the insertion position or the pre-locking position of the pressure element 6 in the receiving part 5. An outer surface 62*d* of the arms may have a contour of a portion of a cylindrical surface.

Adjacent to the bottom end 6*b* of the pressure element 6, an outer surface portion 64 may be tapered, preferably narrowing in a conical shape, which is configured to cooperate with the narrowing portion 53*a* of the receiving part 5.

Between the two arms 62 on the same side of the rod receiving recess 61 and on each side of the rod receiving recess, the outer surface of the pressure element 6 includes substantially planar or flat surface portions 65. The planar surface portions 65 are recessed from the cylindrical outer surface portion 6c of the pressure element to locally narrow a width of the pressure element 6. The recessed planar surface portions 65 together with the recessed portion 58 at the inner surface of the receiving part 5 provide a space for receiving the restraining elements 7 therein and permit the restraining element 7 to be axially displaced relative to the pressure element 6.

Moreover, the two planar surface portions 65 are provided on opposite sides of the longitudinal axis l of the pressure element 6, and a plane of each planar surface portion 65 may be substantially parallel to the longitudinal axis l and the central axis C. Each planar surface portion 65 extends from the rod support surface 61a in the axial direction and ends at or above the narrowing outer surface portion 64 at a distance from the bottom end 6b of the pressure element 6.

An opening 66 is provided at the lower end of each planar surface portion 65, the opening 66 providing access to the head receiving portion 68 and to an inserted head from a direction transverse to the central axis C. More specifically, the opening 66 permits a portion of the restraining element 7 to directly contact the head 3 that is received within the head receiving portion 68, as shown in FIG. 3. The opening 66 may have a semi-circular contour, with a straight line delimiting the opening 66 towards the bottom end 6b. The contour may be provided with rounded edges of the semi-circle. An axial position of the opening 66 is such that when the head 3 is received within the accommodation space of the receiving part, the planar surface portions 3a of the head 3 are located in a region of the openings 66 of the pressure element 6, as shown in FIG. 3.

At a distance from the second end 6b, a circumferentially extending slit 69a is provided. The slit 69a extends around the central axis C of the pressure element 6 along a plane substantially perpendicular to the central axis C. By means of the slit 69a, a ring-shaped portion 69 of the pressure element 6 is formed at its bottom end 6b. The outer surface of the ring-shaped portion 69 forms part of the narrowing outer surface 64 of the pressure element 6. The ring-shaped portion 69 may also serve as a stop for limiting a movement of the restraining element 7 towards the bottom end 6b of the pressure element 6.

The slit 69a may extend along the circumference of the pressure element 6 starting from a first one of the openings 66, extending through the second one of the openings 66, and ending at a distance from the first opening 66, so that a wall portion forming a connection strip 69b is formed between the first opening 66 and a far or opposite end of the slit 69a. The connection strip 69b forms the only connection portion where the ring-shaped portion 69 is integrally connected to the rest of the pressure element 6. The connecting strip 69b has a sufficient length in the circumferential direction so as to provide a stable connection of the ring-shaped portion 69 to the rest of the pressure element 6. At one end of the circumferentially extending slit 69a, there is a substantially vertical slit 69c that extends from the second end 6b fully through the ring-shaped portion 69 into the circumferentially extending slit 69a. The vertical slit 69c together with the ring-shaped portion 69 thus forms a slit ring that is expandable and compressible in the radial direction. When the head 3 of the bone anchoring element 1 is inserted through the opening at the bottom end 6b of the pressure element 6 into the head receiving portion 68, the slit ring expands so that the width of the vertical slit 69c increases, and when the head 3 has been fully inserted into the head receiving portion 68, the slit ring encompasses the head 3 below a position of a largest outer diameter of the head 3 in a direction towards the shank 2.

Figure 12:
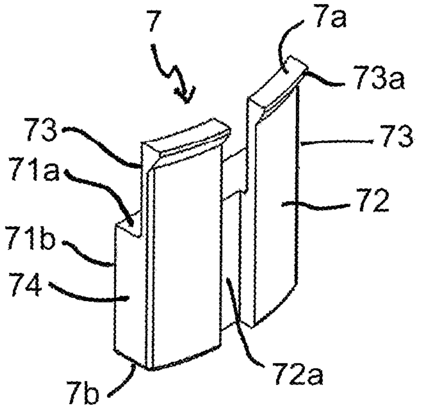
FIG. 12 shows a perspective view from above a restraining element of the bone anchoring device of FIGS. 1 to 3.
Figure 13:
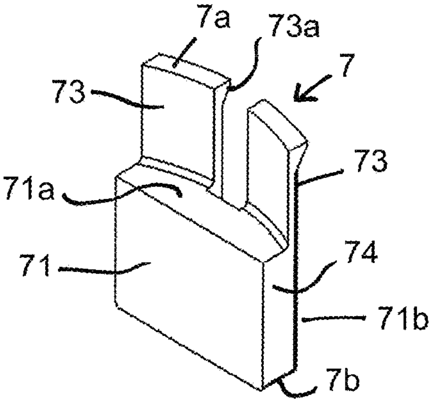
FIG. 13 shows a further perspective view from above the restraining element of FIG. 12.
Figure 14:
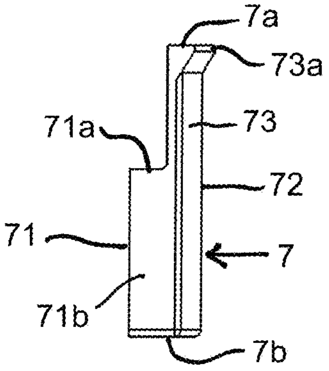
FIG. 14 shows a side view of the restraining element of FIGS. 12 and 13.

Referring now to FIGS. 12 to 14, the restraining element 7 is described. The restraining element 7 preferably is a monolithic part having first end or top end 7a and a second end or bottom end 7b, an outer side facing the receiving part 5 and an opposite inner side facing the pressure element 6 when the restraining element 7 is assembled within the passage 51 of the receiving part 5. The restraining element 7 forms a sliding piece configured to be accommodated in the space formed between the planar surface portion 65 of the pressure element 6 and the recessed portion 58 of the receiving element 7, and to be axially displaced therein.

A length of the restraining element 7 between the top end 7a and the bottom end 7b is such that when the restraining element 7 is at a first or uppermost position with respect to the pressure element 6, wherein the top ends 6a, 7a of the pressure element 6 and the restraining element 7 are at the same axial position, the bottom end 7b of the restraining element 7 is located above the opening 66 of the pressure element 6. When the restraining element 7 is at a second or lowermost position with respect to the pressure element 6, wherein the bottom end 7b of the restraining element abuts on the ring-shaped portion 69 of the pressure element 6 and on the stop 58b formed by the recessed portion 58 of the receiving part 5, the restraining element 7 at least covers the opening 66 of the pressure element 6.

The restraining element 7 generally includes a base portion 71b extending from the bottom end 7b towards the top end 7a and ending at a distance from the top end 7a, and two arms 73 extending from the base portion 71b to the top end 7a. At the inner side of the restraining element 7, the base portion 71b includes a first restraining surface in the form of a substantially planar or flat surface portion 71 that is configured to cooperate with the second restraining surface 3a of the head 3. The arms 73 are thinner than the base portion 71b, thus forming a step 71a at the inner side of the restraining element where the arms 73 protrude from the base portion 71b.

The outer side of the restraining element 7 includes an outer surface portion 72 having a shape of a cylindrical surface portion. When the restraining element 7 and the pressure element 6 are assembled in the passage 51 of the receiving part, the outer surface portion 72 of the restraining element 7 is preferably substantially flush with the outer surface 62d of the arms 62 of the pressure element.

A free end of the arms 73 may have a radially protruding rim 73a, an upper surface of which forms the top end 7a of the restraining element 7. The rim 73a may be similar to the rim 62c of the arms 62 of the pressure element 6, and may be configured to engage the circumferential grooves 57a, 57b provided at the inner surface of the legs 55 of the receiving part 5. The outer surface portion 72 of the restraining element 7 further includes a recessed surface portion 72a extending axially from the step 71a to the bottom end 7b in a region between the two arms 73. A shape of the recessed surface portion 72a when viewed from the outer side of the retaining element may be substantially rectangular. The recessed surface portion 72a serves for receiving a front end of the pin 9 therein, and to guide the front end of the pin 9 in the recessed surface portion 72a when the restraining element 7 is displaced axially relative to the receiving part 5 and the pressure element 6. The engagement of the recessed surface portion 72a by the pin may prevent rotation of the restraining element 7 and the pressure element 6 relative to the receiving part 5.

Lateral sidewalls 74 of the restraining element 7 that extend between the top end 7a and the bottom end 7b may be substantially flat and configured to contact the respective sidewalls 62*a* of the arms 62 of the pressure element 6. Specifically, a width of the restraining element 7 between the two sidewalls 74 may be such that the sidewalls 74 contact the respective sidewalls 62*a* of the arms 62 of the pressure element 6 when the pressure element 6 and the restraining element 7 are assembled within the receiving part 5.

Figure 15:
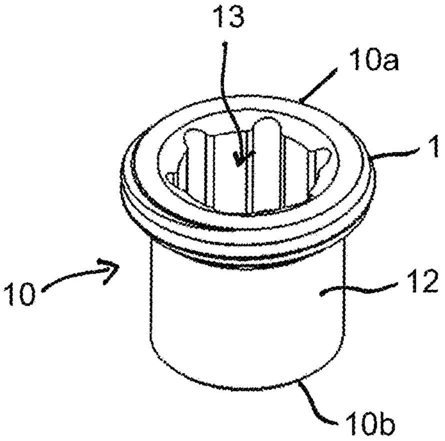
FIG. 15 shows a perspective view from above a plug member of the bone anchoring device of FIGS. 1 to 3.
Figure 16:
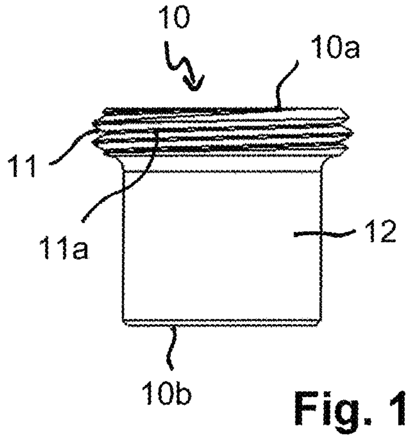
FIG. 16 shows a side view of the plug member of FIG. 15.
Figure 17:
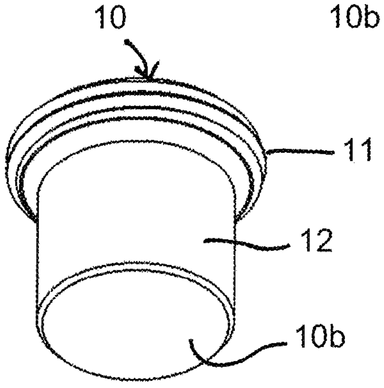
FIG. 17 shows a perspective view from below the plug member of FIGS. 15 and 16.

Referring now to FIGS. 15 to 17, the plug member 10 is described. The plug member 10 preferably is a monolithic part having a first end or top end 10*a* and a second end or bottom end 10*b*. At the top end 10*a* of the plug member 10, a rim portion 11 is formed that has a diameter substantially corresponding to a diameter of the upper portion 67 of the bore of the pressure element 6, and includes an engagement structure in the form of an outer thread 11*a* that is configured to cooperate with the inner thread 67*a* of the pressure element 6. The plug member 10 further includes a substantially cylindrical portion 12 protruding from the rim portion 11 and terminating in a flat circular face that forms the bottom end 10*b* of the plug member 10. The cylindrical portion 12 is shaped so as to be received within the engagement recess 4 of the head 3 of the bone anchoring element 1 and has a smaller diameter than the rim portion 11, so that a stop is formed between the rim portion 11 and the cylindrical portion 12 that serves as an abutment for the free end of the head 3, as shown in FIG. 3. The plug member 10 further has at its top end 10*a* an engagement recess 13 for engagement with a tool, such as a driver.

The parts and portions of the bone anchoring device may be made of any material, preferably, however, of titanium or stainless steel, or of any bio-compatible metal or metal alloy or plastic material. For bio-compatible alloys, a NiTi alloy, for example, Nitinol, may be used. Other materials that can be used are, for example, magnesium or magnesium alloys. Bio-compatible plastic materials that can be used may be, for example, polyether ether ketone (PEEK) or poly-L-lactide acid (PLLA). The parts can be made of the same or of different materials from one another.

Use of the bone anchoring device according to the first embodiment is described, with additional reference to FIGS. 18*a* to 18*d*. In use, the bone anchoring device can be applied as a polyaxial bone anchoring device, as a uniplanar bone anchoring device, or as a monoaxial bone anchoring device.

Figure 18A:
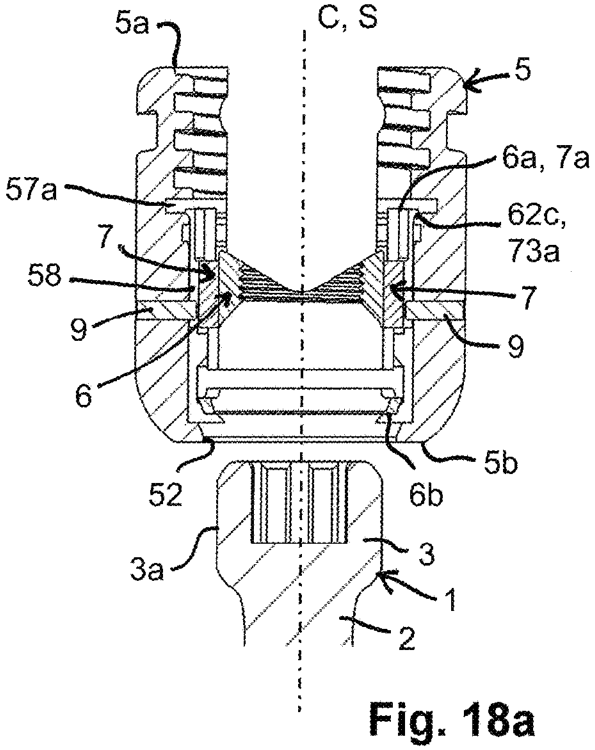
FIG. 18*a* shows a cross-sectional view of the bone anchoring device of FIGS. 1 to 3 without the plug member and with the pressure element at an insertion position before inserting a head of a bone anchoring element into the receiving part.

As shown in FIG. 18*a*, the pressure element 6 and the two restraining elements 7 are pre-assembled with the receiving part 5 such that the pressure element 6 is provided in the passage 51 of the receiving part 5 and the restraining elements 7 are accommodated between the recessed portions 58 at the inner surface of the receiving part 5 and the pressure element 6, and the sidewalls 74 of the restraining elements contact the sidewalls 62*a* of the arms 62 of the pressure element 6. The top ends 6*a*, 7*a* of the pressure element 6 and the restraining elements 7 are substantially at the same axial position, so that the planar surface portions 71 of the restraining elements 7 contact the planar surface portions 65 of the pressure element 6 and are located axially above the openings 66 of the pressure element. Both the upper rims 62*c* and 73*a* of the arms 62, 73 of the pressure element 6 and the restraining elements 7 are held in the first groove 57*a* at the inner surface of the receiving part, which is the insertion position of the pressure element 6. The pins 9 extend through the through-holes 59 of the receiving part 5 into the recessed surface portions 72*a* of the restraining elements 7. Thereby, the restraining elements 7 and the pressure element 6 are secured against rotation within the receiving part 5.

Figure 18B:
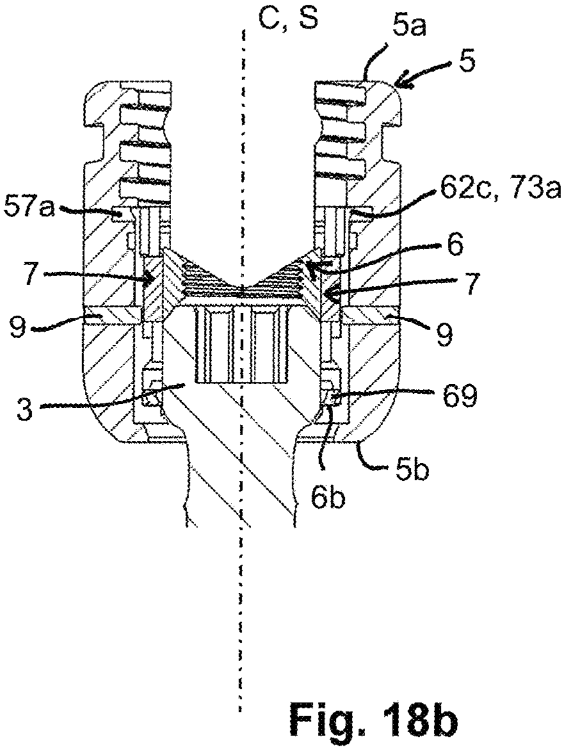
FIG. 18*b* shows a cross-sectional view of the bone anchoring device of FIG. 18*a* after the head has been inserted into the receiving part.

With the pressure element 6 held at the insertion position, the head 3 of the bone anchoring element 1 is inserted from the bottom end 5*b* into the head receiving portion 68 of the pressure element 6. The head 3 is inserted in a position where the substantially planar surface portions 3*a* are circumferentially aligned with the openings 66 of the pressure element 6 and the substantially planar surface portions 71 of the restraining elements 7. This position may be indicated, for example, by indication marks provided at the head and the receiving part (not shown in the figures). During insertion, the ring-shaped portion 69 expands to allow the head 3 to enter the head receiving portion 68, and when the head 3 is fully inserted into the head receiving portion 68, the ring-shaped portion 69 encompasses the head 3 below a position of its largest outer diameter, as shown in FIG. 18*b*. When the head 3 is inserted into the head receiving portion 68 of the pressure element 6, the pressure element 6 and the restraining elements 7 are prevented from moving further towards the top end 5*a* of the receiving part by the upper rims 62*c* and 73*a* of their arms 62, 73 abutting on the upper edge of the first groove 57*a*.

Figure 18C:
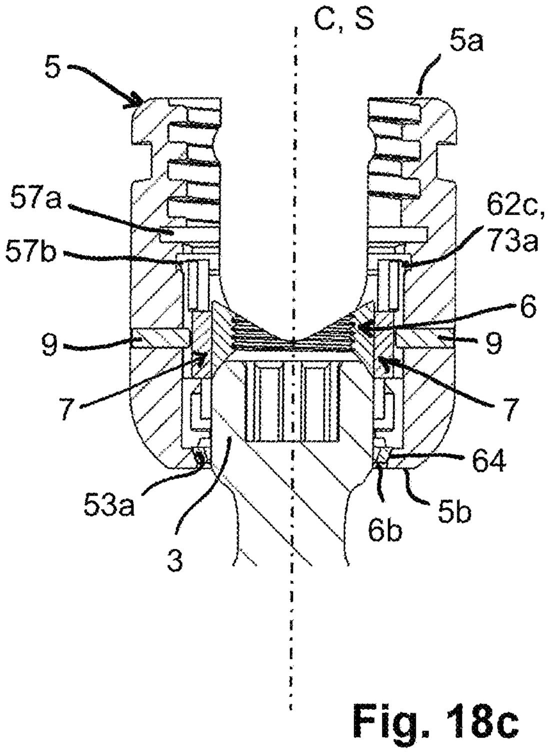
FIG. 18*c* shows a cross-sectional view of the bone anchoring device adjusted from FIG. 18*b* so that the pressure element is at a pre-locking position and the restraining element is at an upper position.

The pressure element 6 together with the restraining elements 7 is then moved towards the bottom end 5*b* of the receiving part 5 to assume a pre-locking position, where the outer rims 62*c*, 73*a* of their arms 62, 73 are held in the second groove 57*b* of the receiving part 5 and the narrowing outer surface portion 64 at the bottom end 6*b* of the pressure element 6 engages the narrowing inner surface portion 53*a* of the receiving part 5, as shown in FIG. 18*c*. The ends of the pins 9 slide along the recessed surface portions 72*a* of the restraining elements 7 when the pressure element 6 together with the restraining elements 7 moves axially downward. In the pre-locking position, the head 3 cannot be removed through the lower opening 52, but is still pivotable in multiple different planes relative to the receiving part 5. When the bone anchoring device is intended to be used as a polyaxial bone anchoring device, the rod 100 is inserted into the U-shaped recess 54 until the rod rests on the rod support surface 61*a* of the pressure element 6. To lock the bone anchoring device, i.e., the head 3 and the rod 100 in the receiving part 5, the locking element 8 is screwed between the legs 55 until the locking element presses onto the rod 100, so that the pressure element 6 is moved further downward until the pressure element clamps the head 3 at a particular angular position with respect to the receiving part 5.

Figure 18D:
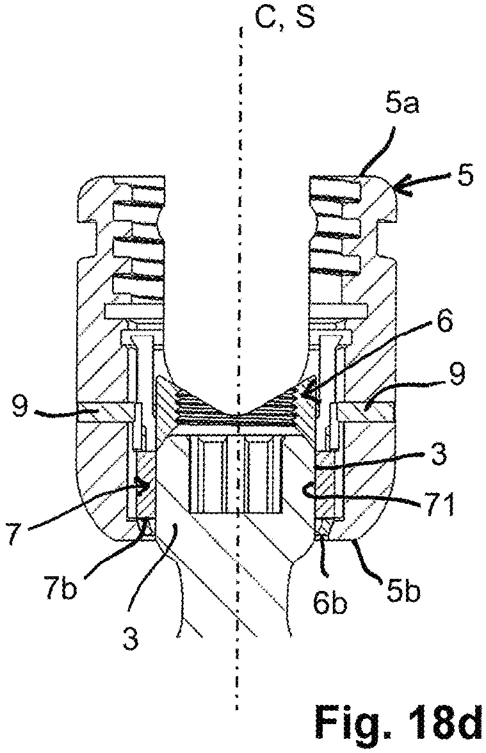
FIG. 18*d* shows a cross-sectional view of the bone anchoring device adjusted from FIG. 18*c* so that the pressure element is at the pre-locking position and the restraining element is at a lower position.

When the bone anchoring device is intended to be used as a uniplanar bone anchoring device, the restraining elements 7 are moved from their uppermost or first position shown in FIG. 18*c* towards the bottom end 6*b* of the pressure element 6 to assume their lowermost or second position shown in FIG. 18*d* prior to insertion of the rod 100. For axial displacement of the restraining elements 7, an instrument (not shown in the figures) may be used that is configured to enter to passage 51 of the receiving part and to press on both restraining elements 7 from above to move the restraining elements towards the bottom ends 5*b*, 6*b* of the receiving part and the pressure element. During the downward movement, the restraining elements 7 are guided and slide along the planar surfaces 65, the sidewalls 62*a* of the arms 62 of the pressure element, and the recessed portions 58 at the inner surface of the receiving part, until the bottom ends 7*b* of the restraining elements abut against the ring-shaped portion 69 of the pressure element and the stop 58*b* formed by the recessed portion 58 of the receiving part 5. In this position of the restraining elements 7, the planar surface portions 71 of the restraining elements 7 are at the axial position of the openings 66 of the pressure element 6, so that the planar surface portions 71 are configured to directly contact the planar surface portions 3*a* of the head 3. Pivoting of the head 3 relative to the receiving part 5 is thus restricted to a single plane parallel to the planar surface portions 71, 3*a* that form the restraining surfaces. In other words, the single plane is spanned by or defined by the central axis C and the channel axis L. Again, the rod 100 can be inserted, and to lock the head 3 and the rod 100 in the receiving part 5, the locking element 8 is screwed between the legs 55 of the receiving part 5 until the locking element presses onto the rod 100 so that the pressure element 6 is moved further downward until the pressure element locks the head 3 at a particular angular position with respect to the receiving part 5 and also locks the rod.

In an alternative manner of use, the restraining elements 7 can already be moved to the lowermost position prior to insertion of the head 3 into the receiving part 5 and the pressure element 6. Thus, the bone anchoring element 1 can be inserted into bone prior to mounting of the receiving part 5 with the pressure element onto the head 3.

When the bone anchoring device is intended to be used as a monoaxial bone anchoring device, i.e., when the axis of the shank 2 is desired to be permanently coaxial with the central axis C of the receiving part 5, the plug member 10 can be used. Before the rod 100 is inserted, the plug member 10 is assembled with the coupling device by screwing the plug member into the inner thread 67*a* of the pressure element 6, where a tool, such as a driver, may be used. In the inserted position of the plug member 10, as shown in FIG. 3, the cylindrical portion 12 is received within the engagement recess 4 of the head 3 of the bone anchoring element 1, so that the shank 2 of the bone anchoring element 1 is prevented from pivoting relative to the receiving part 5 and assumes a zero-angle position relative to the receiving part 5, i.e., the shank axis S of the shank 2 is coaxial with the central axis C. Again, the rod 100 can be inserted and the head 3 and the rod 100 can be locked in the receiving part 5 by screwing the locking element 8 between the legs 55 of the receiving part 5 and tightened.

Referring to FIGS. 19 to 32*d*, a second embodiment of the bone anchoring device is described. Parts and portions that are identical or similar to the first embodiment are provided with the same reference numerals, and the descriptions thereof are not repeated.

Figure 19:
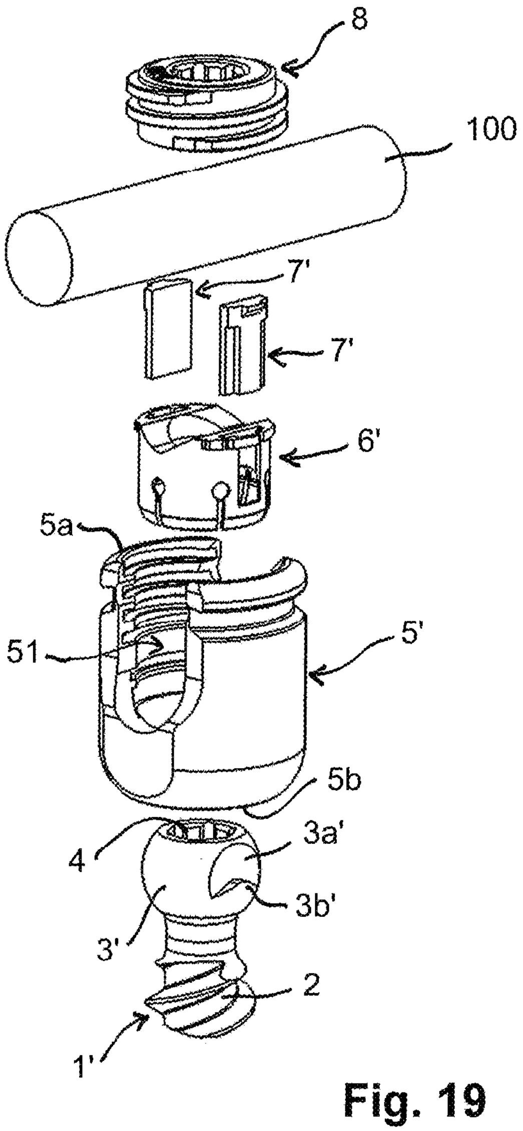
FIG. 19 shows an exploded perspective view of a bone anchoring device according to a second embodiment.
Figure 20:
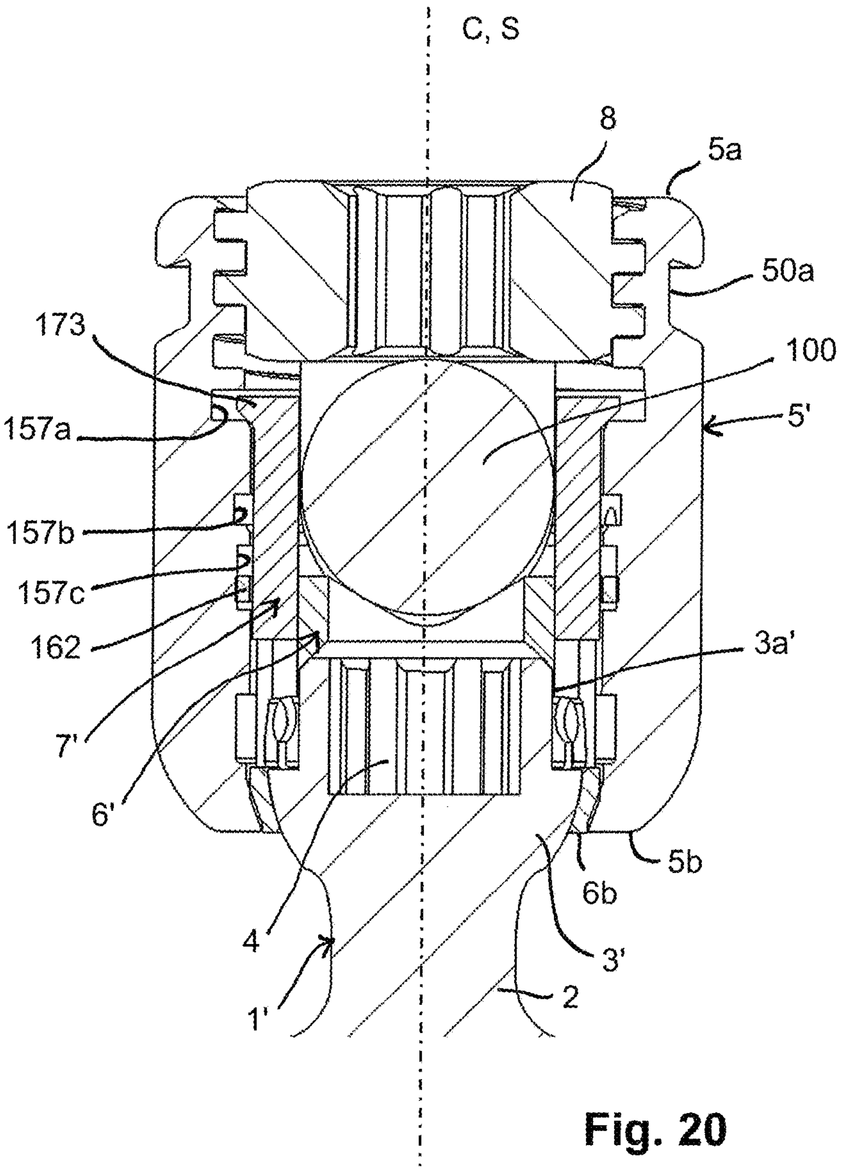
FIG. 20 shows a cross-sectional view of the bone anchoring device of FIG. 19, the cross-section taken in a plane extending through a central axis of the bone anchoring device and perpendicular to a rod axis of an inserted rod.
Figure 21:
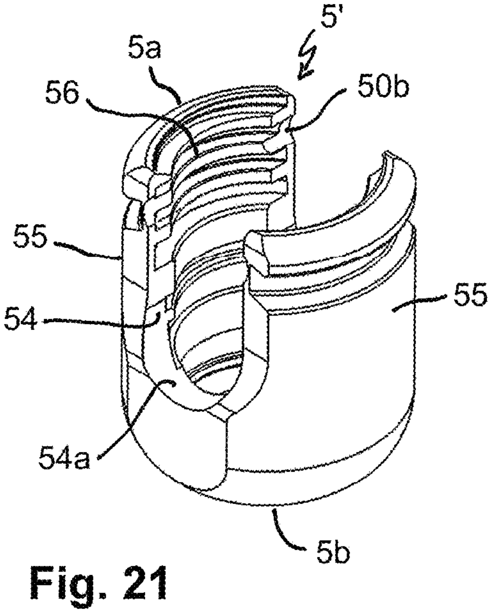
FIG. 21 shows a perspective view from above a receiving part of the bone anchoring device of FIGS. 19 and 20.
Figure 22:
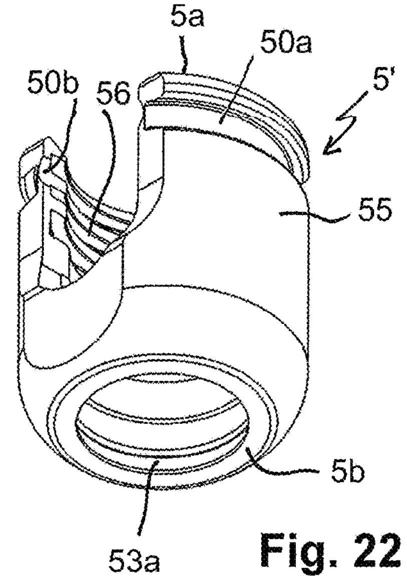
FIG. 22 shows a perspective view from below the receiving part of FIG. 21.
Figure 23:
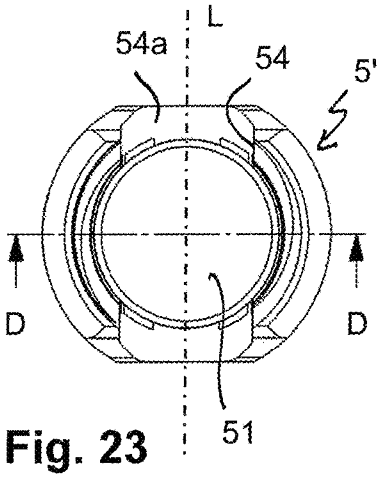
FIG. 23 shows a top view of the receiving part of FIGS. 21 and 22.
Figure 24:
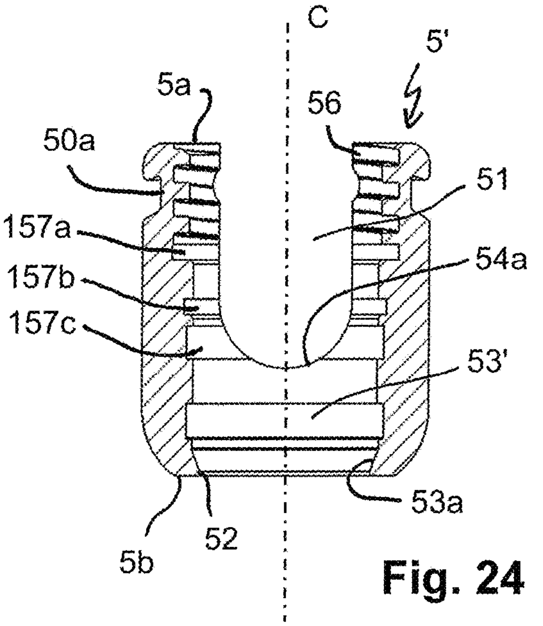
FIG. 24 shows a cross-sectional view of the receiving part of FIGS. 21 to 23, the cross-section taken along line D-D in FIG. 23.
Figure 25:
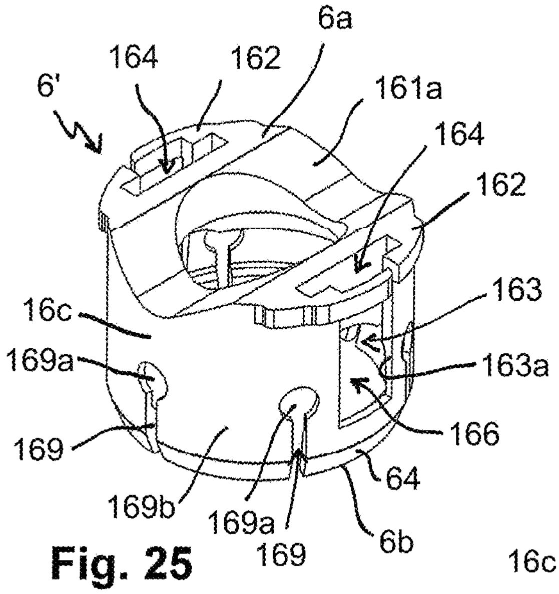
FIG. 25 shows a perspective view from above a pressure element of the bone anchoring device of 19 and 20.
Figure 26:
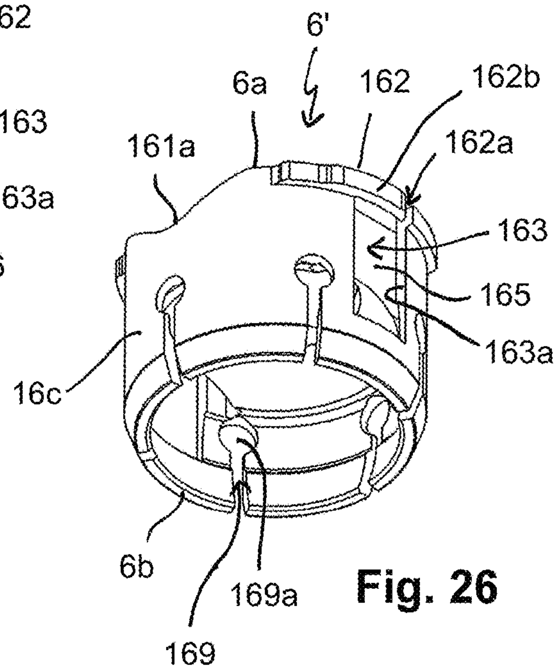
FIG. 26 shows a perspective view from below the pressure element of FIG. 25.
Figure 27:
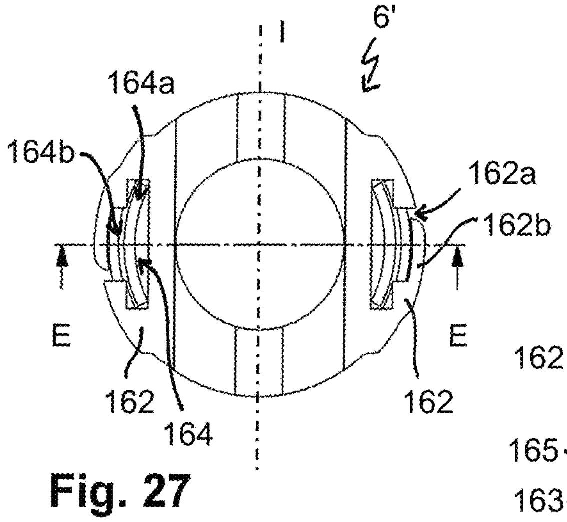
FIG. 27 shows a top view of the pressure element of FIGS. 25 and 26.
Figure 28:
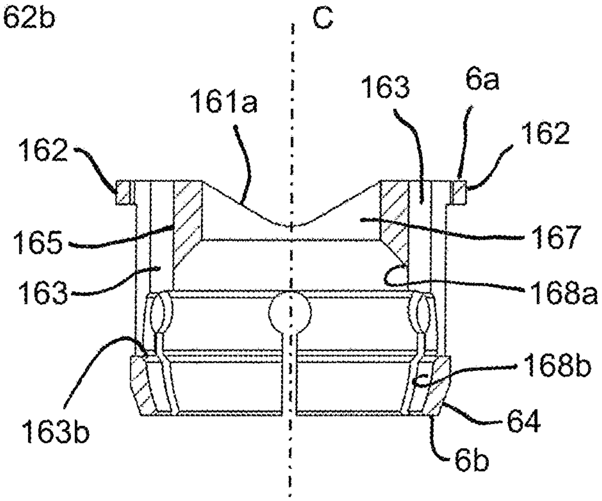
FIG. 28 shows a cross-sectional view of the pressure element of FIGS. 25 to 27, the cross-section taken along line E-E in FIG. 27.

As shown in particular in FIGS. 19 and 20, the bone anchoring device of the second embodiment includes a bone anchoring element 1', a receiving part 5', a pressure element 6', and two restraining elements 7', where the pressure element 6' and restraining elements 7'are configured to be received within the passage 51 that extends from the top end 5*a* to the bottom end 5*b* of the receiving part 5'. As in the first embodiment, the receiving part 5', which may be a monolithic piece, is configured to receive the head 3' of the bone anchoring element 1' and the rod 100 therein, and the pressure element 6' is configured to exert pressure onto the head 3' to clamp the head 3' at a particular angular position relative to the receiving part 5'. The restraining elements 7' are movable relative to the pressure element 6' between a first position and a second position in the axial direction. At the first position, the restraining elements 7' do not act upon the inserted head 3'. Thus, at the first position of the restraining elements 7', the shank 2 of the bone anchoring element 1' may be pivotable in multiple different planes relative to the receiving part 5', i.e., the resulting bone anchoring device is a polyaxial bone anchoring device, while at the second position, the restraining elements 7' may directly contact the inserted head 3' to restrict pivoting of the shank 2 relative to the receiving part 5' within a single plane, i.e., the resulting bone anchoring device is a uniplanar bone anchoring device. To lock the head 3' and the rod 100 in the receiving part 5', a locking element 8 in the form of an inner screw or set screw is provided.

The head 3' of the bone anchoring device of the second embodiment may differ from that of the first embodiment with regard to the shape of the second restraining surfaces. In detail, the second restraining surfaces include substantially planar or flat surface portions 3*a*', and may further be provided with a V-shaped or rounded protrusion 3*b*' at a lower end thereof that may facilitate or assist in pivoting of the head 3' relative to the receiving part 5' in the single plane defined by the first and second restraining surfaces.

Referring in addition to FIGS. 21 to 24, the receiving part 5' has the passage 51 that widens into the accommodation space 53', with the narrowing portion 53*a* provided at the bottom end 5*b* that narrows towards the opening 52 and cooperates with a corresponding surface of the pressure element 6'. The width of the accommodation space 53' is such that the pressure element 6' can expand therein to permit the insertion of the head 3'.

On the inner surface of the legs 55, a circumferential first groove 157*a* is provided at a distance from the bottom 54*a* of the U-shaped recess 54. The first groove 157*a* is provided for engagement with a portion of the restraining elements 7' to hold the restraining elements 7' at an uppermost or first position with respect to the pressure element 6'. At an axial distance from the first groove 157*a* and further towards the bottom end 5*b* of the receiving part 5', a circumferential second groove 157*b* is provided at the inner surface of the legs that serves for engagement with a portion of the restraining elements 7' to hold the restraining elements 7' at a lowermost or second position with respect to the pressure element 6'. Axially further towards the bottom end 5*b* and between the circumferential second groove 157*b* and the accommodation space 53', a circumferential third groove 157*c* is provided for engagement with a portion of the pressure element 6' to secure an insertion position of the pressure element 6'. The third groove 157*c* has an axial dimension that permits an engaged portion of the pressure element 6' to move therein between an insertion position and a pre-locking position.

Referring further to FIGS. 25 to 28, the pressure element 6' is described. The pressure element 6' preferably is a monolithic piece that is configured to be arranged in the passage 51 of the receiving part 5'and to exert pressure onto the inserted head 3'.

The pressure element 6' has a first end or top end 6*a* and a second end or bottom end 6*b*, and may be substantially cylindrical, with a cylindrical outer surface portion 16*c* and an outer diameter that allows the pressure element 6' to move in the passage 51 of the receiving part 5'. In greater detail, the pressure element 6' includes a rod support surface 161*a* and two laterally extending protrusions 162 at the top end 6*a*, and a central bore extending from the rod support surface 161*a* to the bottom end 6*b* along a cylinder axis of the pressure element 6'. A narrowing outer surface portion 64 is provided adjacent to the bottom end 6*b* that may be tapered and is configured to cooperate with the narrowing portion 53*a* of the receiving part 5'. The pressure element 6' further has two pockets 163, each of which is configured to receive at least a portion of the restraining element 7' therein.

The rod support surface 161*a* may have a substantially V-shaped cross-section with a longitudinal axis l extending substantially perpendicular to a cylinder axis of the pressure element 6' which is configured to coincide with the central axis C of the receiving part 5' when the pressure element 6' is in the receiving part 5'.

The two protrusions 162 are provided on opposite sides of the longitudinal axis I. Each protrusion extends radially outward from the cylindrical outer surface portion 16*c*. When the pressure element 6' is assembled within the passage 51 of the receiving part 5', the protrusions are configured to engage the circumferential third groove 157*c* of the receiving part 5' and are movable within the circumferential third groove 157*c* in the axial direction. An upper surface of the protrusion 162 forms the top end 6*a* of the pressure element 6'.

The protrusion 162 has an opening 164 that provides access to the pocket 163 for inserting the restraining element 7'into the pocket 163. The opening 164 has a shape that corresponds to a contour of the restraining element 7' when seen in a cross-section of the restraining element 7', the cross-section taken in a plane perpendicular to an insertion direction of the restraining element 7', i.e., perpendicular to the central axis C. In the present embodiment, the opening 164 includes a first portion 164*a* and a second portion 164*b* that each has a rectangular contour, with the long axes of the rectangles extending parallel to the longitudinal axis l of the rod support surface 161*a*. The first portion 164*a* is closer to the rod support surface 161*a* than the second portion 164*b* and has a greater dimension (i.e., is longer) in a direction parallel to the longitudinal axis l than the second portion 164*b*, so that the opening 164 has a stepped portion. The second portion 164*b* serves to receive a thickened portion of the restraining element 7' therein.

An outer portion of the protrusion 162 that is located farthest away from the longitudinal axis l and is configured to be received within the circumferential third groove 157*c* of the receiving part 5' may be provided with an axial slit 162*a* that extends fully through the protrusion 162 in the axial direction and thus forms a spring portion 162*b* of the protrusion that is resilient in a direction perpendicular to the longitudinal axis l. The edge of the spring portion 162*b* facing the slit 162*a* may be rounded.

The central bore of the pressure element 6'has an upper portion 167 adjacent the rod support surface 161*a* that widens into a head receiving portion 168 adjacent the bottom end 6*b*, wherein the head receiving portion 168 is configured to receive the head 3' of the bone anchoring element 1'. The upper portion 167 may be substantially cylindrical with a diameter smaller than a diameter of the head receiving portion 168. The head receiving portion 168 forms an opening at the bottom end 6*b* for inserting the head 3', and includes an upper spherical section 168*a* and a lower spherical section 168*b* that are shaped so as to matingly receive the spherical head 3' therein, to encompass the head 3' laterally and from a free end of the head, and to cover a portion of the head including a largest diameter of the head.

The head receiving portion 168 has a plurality of slits 169 that are open to the bottom end 6*b* and that extend from the bottom end 6*b* to a distance thereof in the axial direction. Each slit 169 may terminate in an enlarged end portion, such as a circular opening 169*a*. The slits 169 are spaced apart from one another in a circumferential direction of the pressure element 6', thus forming a plurality of wall sections 169*b* between them that render the head receiving portion 168 compressible and expandable.

The two pockets 163 of the pressure element 3' are provided on opposite sides of the longitudinal axis l, axially below the openings 164 of the protrusions 162. Each pocket 163 extends from the top end 6*a* of the pressure member in the axial direction and ends at a distance from the bottom end 6*b*, preferably above the narrowing portion 64. The pocket 163 is accessible through the opening 164 of the protrusion 162 at the top end 6*a*, and is closed towards the bottom end 6*b* by a stop 163*b* that may be formed by a wall of the cylindrical outer surface portion 16*c* of the pressure element 6'.

The pocket 163 is delimited towards the central bore by a substantially planar or flat surface portion 165 that may be similar to the substantially planar or flat surface portion 65 of the pressure element 6 of the first embodiment. Like in the first embodiment, an opening 166 is provided at the lower end of the planar surface portion 165, the opening 166 providing access to the head receiving portion 168 and to an inserted head, to permit the first restraining surface at the restraining element 7' to directly contact the inserted head 3'. The opening 166 may have a semi-circular contour with a straight line delimiting the opening 166 towards the bottom end 6*b*, and a circular arc of the contour extending from the straight line towards the top end 6*a*. The contour may be provided with rounded edges of the semi-circle. An axial position of the opening 166 is such that when the head 3'is received within the accommodation space of the receiving part, the planar surface portions 3*a'* of the head 3' are located in a region of the openings 166 of the pressure element 6'.

The cylindrical outer surface portion 16*c* delimits the pocket 163 towards the outside of the pressure element 6'. An opening 163*a* is provided in the cylindrical outer surface portion 16*c* that permits a thickened portion of the restraining element 7' to extend there through when the restraining element is received within the pocket 163. The opening 163*a* has a substantially rectangular contour when viewed from the outer surface of the pressure element, and extends from the protrusion 162 to the stop 163*b* that delimits the pocket towards the bottom end 6*b*. A position and dimension of the opening 163*a* in the circumferential direction of the pressure element is the same as the position and dimension of the second portion 164*b* of the opening 164 in the circumferential direction, i.e., parallel to the longitudinal axis l.

Figure 29:
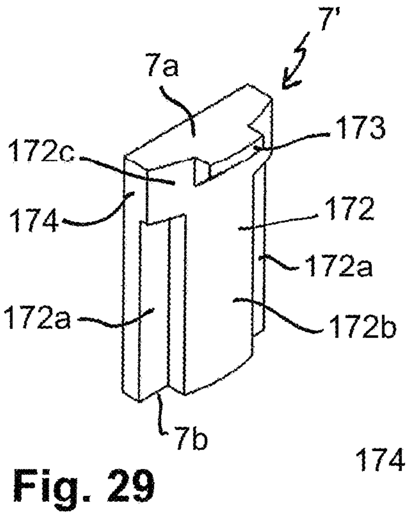
FIG. 29 shows a perspective view from above a restraining element of the bone anchoring device of FIGS. 19 and 20.
Figure 31:
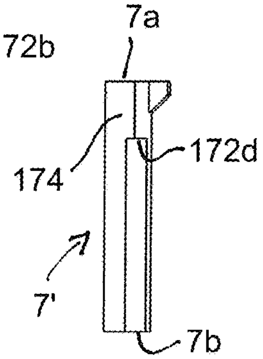
FIG. 31 shows a side view of the restraining element of FIGS. 29 and 30.
Figure 30:
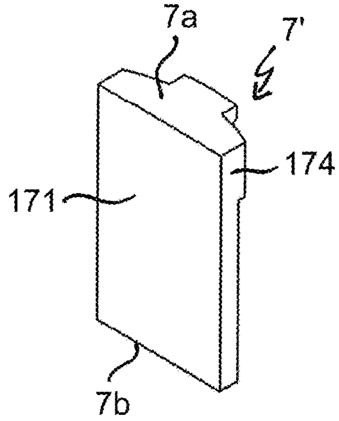
FIG. 30 shows a further perspective view from above the restraining element of FIG. 29.

Referring now to FIGS. 29 to 31, the restraining element 7'is described. The restraining element 7' is a preferably monolithic part having a first end or top end 7*a* and a second end or bottom end 7*b*, an outer side facing the receiving part 5' and an opposite inner side facing the pressure element 6' and/or an inserted head when the restraining element 7' is assembled within the passage 51 of the receiving part 5', and sidewalls 174 extending between the inner and outer sides and between the top and bottom ends. Generally, the restraining element 7' is a sliding piece configured to be at least partially received within the pocket 163 of the pressure element 6' and to be axially displaced therein.

The restraining element 7' is a substantially rectangular part with a substantially planar or flat surface portion 171 at its inner side that serves as a first restraining surface configured to cooperate with the second restraining surface 3*a'* of the head 3', and an outer surface portion 172 having a shape of a cylindrical surface portion. The outer surface portion 172 includes two recessed portions 172*a* each extending from the bottom end 7*b* towards the top end 7*a*, and ending at a distance from the top end 7*a*. A shape of the recessed portion 172*a* when viewed from the outer side of the retaining element may be substantially rectangular. The recessed portions 172*a* locally reduce a thickness of the restraining element 7' between its inner side and outer side and are located laterally at the outer sides of the outer surface portion 172 adjacent the sidewalls 174, thus forming a first thickened portion 172*b* between them that is located approximately in the middle of the restraining element 7'. The first thickened portion 172*b* is configured to be received within the second portion 164*b* of the opening 164 and the opening 163*a* of the cylindrical outer surface portion 16*c* of the pressure element 6', preferably such that the outer surface of the first thickened portion 172*b* is flush with the cylindrical outer surface portion 16*c* of the pressure element 6' when the restraining element 7' is received within the pocket 163. The recessed portions 172*a* of the restraining element 7' are configured to be insertable through the first portion 164*a* of the opening 164 into the pocket 163 of the pressure element 6'. Generally, a thickness of the restraining element 7' between its inner side and outer side is such that the restraining element 7' is configured to be inserted through the opening 164 and received within the pocket 163 of the pressure element 6'.

Further, by means of the recessed portions 172*a* ending at a distance from the top end 7*a*, a second thickened portion 172*c* is formed adjacent the top end 7*a* of the restraining element 7', the second thickened portion 172*c* extending along the entire width of the restraining element 7' between its sidewalls 174. The first and second thickened portions 172*b*, 172*c* together form a T-shaped thickened portion of the restraining element 7'. A step 172*d* is formed between the recessed portions 172*a* and the second thickened portion 172*c*, which is configured to abut on the protrusion 162 of the pressure element 6' when the restraining element 7'is adjusted to a lowermost or second position with respect to the pressure element 6', e.g., when the restraining element is fully inserted into the pocket 163. The step 172*d* may also serve as a stop for limiting the movement of the restraining element 7' relative to the pressure element 6' towards its bottom end 6*b*. A dimension of the recessed portions 172*a* from the bottom end 7*b* to the step 172*d* is preferably the same as a dimension of the pocket 163 from the top end 6*a* of the pressure element 6' to the stop 163*b* that delimits the pocket towards the bottom end 6*b*.

In addition, a radially protruding rim or protrusion 173 is provided on the second thickened portion 172*c* at the top end 7*a* of the restraining element 7'. The protrusion 173 may be configured to engage the circumferential first and second grooves 157*a*, 157*b* provided at the inner surface of the legs 55 of the receiving part 5'. In particular, when the restraining elements 7' are at an uppermost or first position with respect to the pressure element 6', the protrusions 173 may be held in the circumferential first groove 157*a* of the receiving part 5', and when the restraining elements 7' are at a lowermost or second position with respect to the pressure element 6', the protrusions 173 may be held in the circumferential second groove 157*b*, to secure the first and second positions, respectively.

Use of the bone anchoring device of the second embodiment is described, with additional reference to FIGS. 32*a* to 32*d*. In use, the bone anchoring device can be applied as a polyaxial bone anchoring device or as a uniplanar bone anchoring device.

Figure 32A:
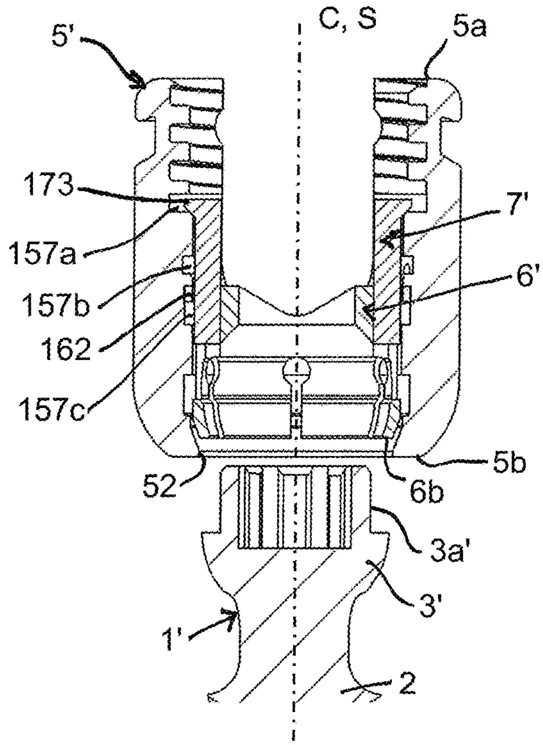
FIG. 32*a* shows a cross-sectional view of the bone anchoring device of FIGS. 19 and 20 with the pressure element at an insertion position prior to inserting a head of a bone anchoring device into the receiving part.

As shown in FIG. 32*a*, the pressure element 6' and the two restraining elements 7' are pre-assembled with the receiving part 5', such that the pressure element 6' is provided in the passage 51 of the receiving part 5'with its protrusions 162 being held in the third groove 157*c* at the inner surface of the receiving part 5'. The restraining elements 7' are inserted into the pockets 163 of the pressure element 6' at their uppermost or first positions where their protrusions 173 are held in the first groove 157*a* at the inner surface of the receiving part and their bottom ends 7*b* are located axially above the stop 163*b* of the pocket, so that the planar surface portions 171 of the restraining elements 7'are located at the planar surface portions 165 and axially above the openings 166 of the pressure element 6'.

Figure 32B:
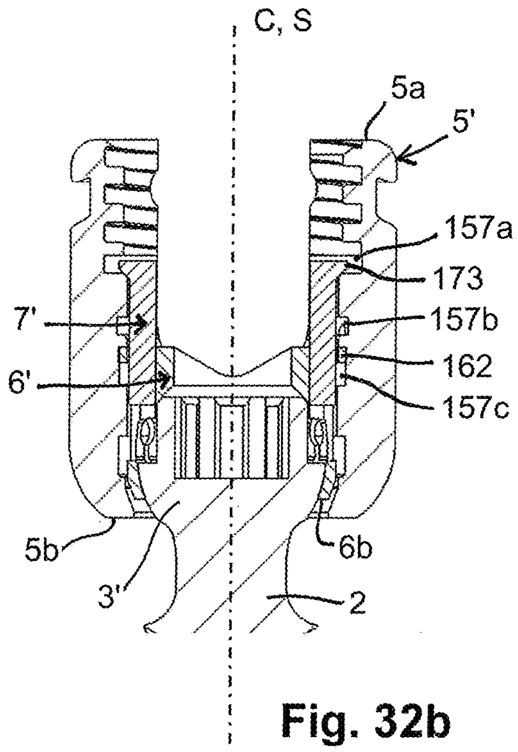
FIG. 32*b* shows a cross-sectional view of the bone anchoring device of FIG. 32*a* after the head has been inserted into the receiving part.

The head 3' of the bone anchoring element 1'is inserted from the bottom end 5*b* into the head receiving portion 168 of the pressure element 6'. The head receiving portion 168 expands due to the presence of the slits 169 to allow the head 3' to enter the head receiving portion 168. During insertion of the head 3', the pressure element 6' is prevented from moving further towards the top end 5*a* of the receiving part 5' by the protrusions 162 abutting the upper edge of the third groove 157*c*. FIG. 32*b* shows the state of the bone anchoring device with the head 3' fully inserted.

Figure 32C:
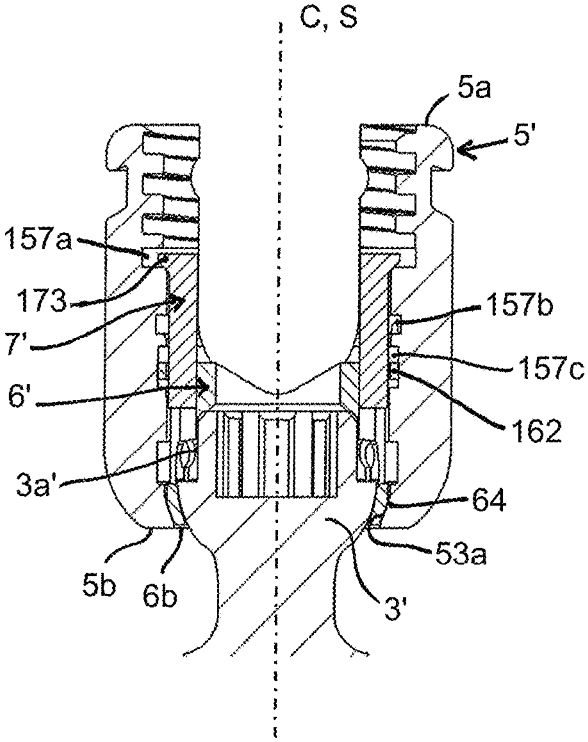
FIG. 32*c* shows a cross-sectional view of the bone anchoring device adjusted from FIG. 32*b* so that the pressure element is at a pre-locking position and the restraining element is at an upper position.

The pressure element 6' is then moved towards the bottom end 5*b* of the receiving part 5' to assume a pre-locking position where the narrowing outer surface portion 64 at the bottom end 6*b* of the pressure element 6' engages the narrowing inner surface portion 53*a* of the receiving part 5'as shown in FIG. 32*c*. In the pre-locking position, the head 3' cannot be removed through the lower opening 52 but is still pivotable in multiple different planes relative to the receiving part 5'. When the bone anchoring device is intended to be used as a polyaxial bone anchoring device, the rod 100 is inserted into the U-shaped recess 54 until the rod rests on the rod support surface 161*a* of the pressure element 6'. To lock the bone anchoring device, i.e., the head 3' and the rod 100 in the receiving part 5', the locking element 8 is screwed between the legs 55 and tightened to lock the head and the rod.

Figure 32D:
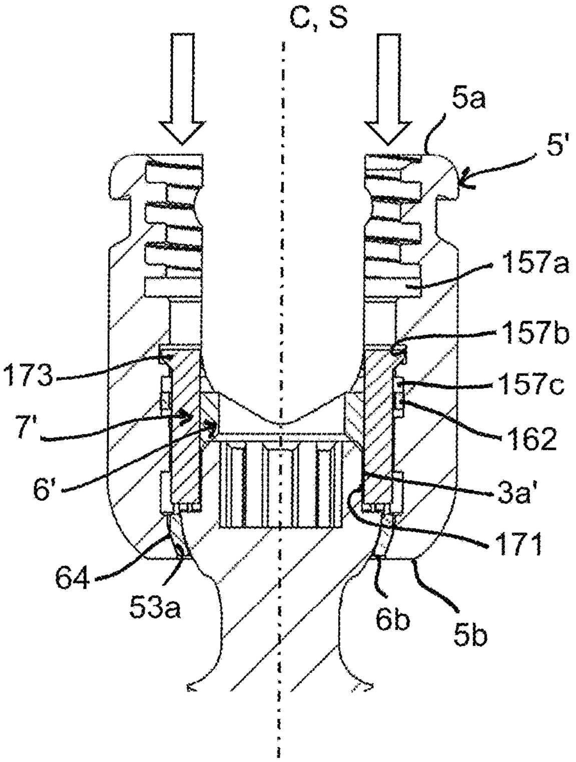
FIG. 32*d* shows a cross-sectional view of the bone anchoring device adjusted from FIG. 32*c* so that the pressure element is at the pre-locking position and the restraining element is at a lower position.

When the bone anchoring device is intended to be used as a uniplanar bone anchoring device, the restraining elements 7' are moved from their uppermost or first position shown in FIG. 32*c* downward into their lowermost or second position shown in FIG. 32*d* before the rod 100 is inserted. Moving of the restraining elements 7' into the second position can be effected when the pressure element 6' is either in the insertion position or the pre-locking position. For axial displacement of the restraining elements 7', an instrument (not shown in the figures) may be used that is configured to enter to passage 51 of the receiving part and to press on both restraining elements 7' from above to move the restraining elements within the pockets 163 of the pressure element 6' towards the bottom end 6*b*. The downward movement causes the protrusions 173 to disengage from the first groove 157*a* of the receiving part 5' and to engage the second groove 157*b*. During the downward movement, the restraining elements 7' are guided and slide along the planar surfaces 165 within the pockets 163 of the pressure element until their bottom ends 7*b* abut on the stop 163*b* at the bottom of the pocket and/or the steps 172*d* abut on the protrusions 162 of the pressure element 6'. In this position of the restraining elements 7', the planar surface portions 171 are at the axial position of the openings 166 of the pressure element 6', so that the planar surface portions 171 are configured to directly contact the planar surface portions 3*a'* of the head 3'. Pivoting of the head 3' relative to the receiving part 5' is thus restricted to a single plane parallel to the planar surface portions 171, 3*a'* that form the restraining surfaces. In other words, the single plane is spanned by or defined by the central axis C and the channel axis L. Again, the rod 100 can be inserted and the locking element 8 is screwed between the legs 55 of the receiving part 5' and tightened to lock the head and the rod.

Additional modifications of the above-described embodiments are also conceivable. In particular, the shapes of the parts are not limited to the detailed shapes shown in the figures. Deviations may be possible and are encompassed by the present disclosure. Although in the embodiments two restraining elements are provided, only one retaining element or more than two retaining elements may be provided. Features described in connection with the bone anchoring device of the first embodiment may also be applied to the second embodiment, and vice versa. For example, the bone anchoring device of the second embodiment may also be provided with the plug member of the first embodiment to obtain a monoaxial bone anchoring device.

Instead of the locking element 8 being a set screw, all other kinds of locking assemblies known in the art may be used. For the bone anchoring element, all types of bone anchoring elements that are suitable for anchoring in bone or a vertebra, such as bone screws, bone nails, etc. may be used. As used in the present specification and the appended claims, the term "rod" shall be understood as including any elongate member, regardless of the cross-sectional shape of the elongate member. Specifically, a spinal stabilization rod as used herein may have a substantially circular, oval, or angular cross-section. Such a cross-section may further vary along a length of the rod. The rod may be stiff or flexible.

Moreover, the accommodation space of the receiving part and the pressure element may have a design that allows pivoting of the bone anchoring element to a greater pivot angle to one side as compared to other sides.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:

a bone anchoring element having a shank for anchoring to bone and a head;

a receiving part having a first end, a second end below the first end, a central axis that extends between the first and second ends, and an accommodation space at the second end for pivotably accommodating the head of the bone anchoring element;

a monolithic pressure element movable in the receiving part and comprising a rod contacting surface for engaging a rod that is connectable to the receiving part and a head contacting surface configured to engage and exert pressure on the head to clamp the head at an angular position relative to the receiving part, wherein the pressure element defines at least one opening that provides access laterally through the pressure element to the head when the pressure element engages the head in the receiving part; and at least one restraining element separate from the pressure element and positionable in the receiving part, wherein the restraining element is engageable with and movable relative to the pressure element and comprises a first restraining surface configured to engage the head laterally through the opening of the pressure element to restrict the pivoting of the head relative to the receiving part in at least one radial direction relative to the central axis while the head remains pivotable in at least one other radial direction relative to the central axis.

2. The bone anchoring device of claim 1, wherein when the head, the pressure element, and the restraining element are assembled to the receiving part, the restraining element is movable from a first position where the shank of the bone anchoring element is pivotable in multiple different planes relative to the receiving part, to a second position where the first restraining surface of the restraining element engages the head to restrict pivoting of the shank relative to the receiving part within a single plane.

3. The bone anchoring device of claim 1, wherein the first restraining surface of the restraining element is engageable with a corresponding second restraining surface at the head of the bone anchoring element to restrict the pivoting of the bone anchoring element.

4. The bone anchoring device of claim 3, wherein when the head, the pressure element, and the restraining element are assembled to the receiving part, the restraining element is positionable in the receiving part such that the first restraining surface of the restraining element remains spaced apart from the head.

5. The bone anchoring device of claim 3, wherein at least one of the first restraining surface or the second restraining surface comprises a planar surface.

6. The bone anchoring device of claim 1, wherein the at least one restraining element comprises two restraining elements that are configured to be offset from one another by 180° in the receiving part.

7. The bone anchoring device of claim 1, wherein at least one of the pressure element or the receiving part comprises a guiding surface configured to guide the movement of the restraining element in the receiving part.

8. The bone anchoring device of claim 1, wherein an upper end of the restraining element is positionable at a same axial position as an upper end of the pressure element in the receiving part.

9. The bone anchoring device of claim 1, wherein a stop on the pressure element and/or the receiving part limits the downward movement of the restraining element towards the second end of the receiving part.

10. The bone anchoring device of claim 1, further comprising a plug member configured to engage the head of the bone anchoring element in the receiving part to form a monoaxial connection where the bone anchoring element is prevented from pivoting relative to the receiving part.

11. The bone anchoring device of claim 10, wherein a first portion of the plug member is engageable with a bore of the pressure element, and a second portion that extends from the first portion to engage a drive recess on the head of the bone anchoring element.

12. The bone anchoring device of claim 1, wherein the pressure element comprises a head receiving portion configured to extend below a portion of the head having a greatest diameter measured in a direction perpendicular to the central axis when the head and the pressure element are in the receiving part.

13. The bone anchoring device of claim 1, wherein the pressure element is configured to be held at a first position where the head is insertable into the accommodation space, and is movable from the first position to and configured to be held at a second position where the head is prevented from being removed from the accommodation space.

14. The bone anchoring device of claim 1, wherein when the head, the pressure element, and the restraining element are assembled to the receiving part, the first restraining surface of the restraining element is movable in a direction parallel to the central axis in the receiving part to engage the head.

15. A method of adjusting a bone anchoring device comprising a bone anchoring element having a shank for anchoring to bone and a head, a receiving part having a first end, a second end below the first end, a central axis that extends between the first and second ends, and an accommodation space at the second end for pivotably accommodating the head of the bone anchoring element, a monolithic pressure element movable in the receiving part and comprising a rod contacting surface for engaging a rod that is connectable to the receiving part and a head contacting surface configured to engage and exert pressure on the head to clamp the head at an angular position relative to the receiving part, wherein the pressure element defines at least one opening that provides access laterally through the pressure element to the head when the pressure element engages the head in the receiving part, and at least one restraining element separate from the pressure element and engageable with and movable relative to the pressure element in the receiving part, the method comprising:

inserting the head of the bone anchoring element from the second end of the receiving part into the accommodation space when the pressure element is at an insertion position relative to the receiving part;

adjusting the pressure element from the insertion position to a pre-locking position where the head is prevented from being removed from the accommodation space; and selectively moving the restraining element relative to the pressure element from a first position where the restraining element is spaced apart from the head in the receiving part and the head is pivotable relative to the receiving part, to a second position where a first restraining surface of the restraining element engages the head laterally through the opening of the pressure element to restrict the pivoting of the head relative to the receiving part in at least one radial direction relative to the central axis while the head remains pivotable in at least one other radial direction relative to the central axis.

16. The method of claim 15, wherein the shank of the bone anchoring element is pivotable in multiple different planes relative to the receiving part when the restraining element is at the first position, and pivoting of the shank relative to the receiving part is restricted within a single plane when the restraining element is at the second position.

17. A bone anchoring device comprising:

a bone anchoring element having a shank for anchoring to bone and a head with a spherical segment-shaped outer surface;

a receiving part having a first end, a second end below the first end, a central axis that extends between the first and second ends, and an accommodation space at the second end for pivotably accommodating the head of the bone anchoring element;

a monolithic pressure element movable in the receiving part and comprising a rod contacting surface for engaging a rod that is connectable to the receiving part and a head contacting surface configured to extend below a portion of the head having a greatest diameter measured in a direction perpendicular to the central axis and to engage the spherical segment-shaped outer surface of the head to exert pressure on the head to clamp the head at an angular position relative to the receiving part; and at least one restraining element separate from the pressure element and movable in the receiving part, the restraining element comprising a restraining surface configured to engage the head to restrict the pivoting of the head relative to the receiving part in at least one radial direction relative to the central axis while the head remains pivotable in at least one other radial direction relative to the central axis.

18. The bone anchoring device of claim 17, wherein at least one opening is formed in a wall of the pressure element, and wherein the restraining element is movable to a position where the restraining surface of the restraining element extends laterally through the opening to engage the head.

19. The bone anchoring device of claim 17, wherein an outer surface of the pressure element and an inner surface of the receiving part are configured to cooperate in a manner such that moving the pressure element towards the second end of the receiving part compresses at least part of the head contacting surface of the pressure element to clamp the head in the receiving part.

20. The bone anchoring device of claim 17, wherein when the head, the pressure element, and the restraining element are assembled to the receiving part, the restraining element is movable from a first position where the shank of the bone anchoring element is pivotable in multiple different planes relative to the receiving part, to a the second position where the restraining surface of the restraining element engages the head to restrict pivoting of the shank relative to the receiving part within a single plane.

* * * * *